United States Patent
Grau-Campistany et al.

(10) Patent No.: US 12,161,745 B2
(45) Date of Patent: Dec. 10, 2024

(54) PEPTIDES AND COMPOSITIONS FOR USE IN COSMETICS

(71) Applicant: LIPOTRUE, S.L., Gava (ES)

(72) Inventors: Ariadna Grau-Campistany, Barcelona (ES); Silvia Pastor, Alicante (ES); Patricia Carulla, Barcelona (ES); Juan Carlos Escudero, Barcelona (ES); Julia A. Boras, Begas (ES); Marco Jan Klein, L'Hospitalet de Llobregat (ES)

(73) Assignee: LIPOTRUE, S.L., Gava (ES)

( * ) Notice: Subject to any disclaimer, the term of this patent is extended or adjusted under 35 U.S.C. 154(b) by 714 days.

(21) Appl. No.: 17/433,860

(22) PCT Filed: Mar. 26, 2020

(86) PCT No.: PCT/EP2020/058463
§ 371 (c)(1),
(2) Date: Aug. 25, 2021

(87) PCT Pub. No.: WO2020/193673
PCT Pub. Date: Oct. 1, 2020

(65) Prior Publication Data
US 2022/0142899 A1 May 12, 2022

(30) Foreign Application Priority Data
Mar. 28, 2019 (EP) .................................. 19382222

(51) Int. Cl.
*A61K 8/64* (2006.01)
*A61Q 19/08* (2006.01)
*C07K 5/117* (2006.01)

(52) U.S. Cl.
CPC ............. *A61K 8/64* (2013.01); *A61Q 19/08* (2013.01); *C07K 5/1024* (2013.01)

(58) Field of Classification Search
CPC ......... A61K 8/64; A61Q 19/08; C07K 5/1024
See application file for complete search history.

(56) References Cited

U.S. PATENT DOCUMENTS

2007/0197444 A1* 8/2007 Herman ............. C12N 15/1037
514/21.4

FOREIGN PATENT DOCUMENTS

| WO | 2011047868 A2 | 4/2011 |
| WO | 2018154080 A1 | 8/2018 |

OTHER PUBLICATIONS

J.R. Holder, et al; Structure-activity relationships of the melanocortin tetrapeptide Ac—His-D-Phe-Arg-Trp-NH2 at the mouse melanocortin receptors . . . ; Journal of Medicinal Chemistry; vol. 45; No. 26; Dec. 2002; pp. 5736-5744; XP002302531.
F. Gorouhi, et al; Role of topical peptides in preventing or treating aged skin; International Journal of Cosmetic Science; vol. 31; Jan. 2009; pp. 327-345; XP007909646.
A. Todorovic, et al; Discovery of melanocortin ligands via a double simultaneous substitution strategy based on the Ac—His-DPhe-Arg-Trp-NH2 template; ACS Chemical Neoroscience; vol. 9; No. 11; May 2018; pp. 2753-2766; XP055617748.
International Search Report for PCT/EP2020/058463 dated Jul. 16, 2020.

* cited by examiner

*Primary Examiner* — Li N Komatsu
(74) *Attorney, Agent, or Firm* — LUCAS & MERCANTI, LLP

(57) ABSTRACT

A family of peptides which are able to increase synthesis of homeodomain protein Mohawk and useful as anti-aging agents and as rejuvenating agents.

9 Claims, 8 Drawing Sheets

Specification includes a Sequence Listing.

(A)

(B)

(C)

PEPTIDES AND COMPOSITIONS FOR USE IN COSMETICS

CROSS-REFERENCE TO RELATED APPLICATIONS

This application is a 371 of PCT/EP2020/058463, filed Mar. 26, 2020, which claims the benefit of European Patent Application No. 19382222.8 filed Mar. 28, 2019, each of which are incorporated herein by reference.

REFERENCE TO A SEQUENCE LISTING SUBMITTED ELECTRONICALLY AND INCORPORATION BY REFERENCE OF THE CONTENTS OF THE ELECTRONIC SUBMISSION

An electronic submission, containing the Sequence Listing for SEQ ID NO:1 and SEQ ID NO: 2 disclosed herein, and in computer readable form, as well as a paper copy of the Sequence Listing, are submitted herewith, are hereby referred to herein, and are hereby incorporated by reference herein in their entireties, including the contents thereof.

BACKGROUND OF THE INVENTION

The present invention relates to the field of molecular biology, more precisely to molecular biology applied to cosmetics, even more precisely to peptides and compositions comprising said peptides able to increase the expression and the synthesis of Mohawk.

In the last decades life expectancy of the population has increased significantly. In addition, there is also an increased concern in the population regarding personal aesthetics and to try to delay or minimize the appearance of signs related to aging.

The skin is the largest organ in humans and due to its location, in the body interface, is subject to intrinsic (chronologic) aging and extrinsic aging. Skin aging is a complex biological process influenced by combination of endogenous and exogenous factors (endogenous: genetics, cellular metabolism, hormone and metabolic processes; exogenous: chronic light exposure, pollution, ionizing radiation, chemicals, toxins) and, hence, lead to changes in the skin and to the appearance of imperfections therein (for example, loss of firmness, wrinkling, roughness and/or sagginess).

These factors induce cumulative structural and physiological alterations at the different layers of the skin as well as changes in overall skin appearance (Ganceviciene, R., Liakou, A. I., Theodoridis, A., et al. (2012) *Skin Anti-Aging Strategies*. Dermato-Endocrinology, 4, 308-319).

Three primary structural components of the dermis are collagen, elastin and Glycosaminoglycans (GAGs), which have been the subjects of the majority of anti-aging research and efforts for aesthetic-anti-aging strategies pertaining to the skin, which range from "anti-wrinkle creams" to various filling agents (Baumann, L. (2007), *Skin ageing and its treatment*. J. Pathol., 211, 241-251.).

Collagens constitute a large family of extracellular matrix (ECM) proteins that play a fundamental role in supporting the structure of various tissues in multicellular animals. The mechanical strength of fibrillar collagens is highly dependent on the formation of covalent cross-links between individual fibrils, a process initiated by the enzymatic action of members of the lysyl oxidase (LOX) family. The biosynthesis of collagen is a highly complicated process involving numerous steps, including chain association and folding, secretion, procollagen processing and cross-linking. As exemplified for human type collagen, a heterotrimeric molecule composed of two α 1 and one α 2 chains, after synthesis on the ribosome and their import into the rough endoplasmic reticulum, collagen chains are subjected to a series of post-translational modifications resulting in the assembly of procollagen chains (Rodriguez-Pascual, F., Slatter, D. A. (2016) *Collagen cross-linking: insights on the evolution of metazoan extracellular matrix*. Scientific Reports, 6, 37374.).

In addition, collagens are the most abundant proteins of the body (70% by dry weight) and consist primarily of the fibrillar type I collagen and type III collagen, which together provide the majority of the strength and stiffness of the tissue. Although the minor collagens make up less than 10% of the total collagen content, they play a key role in ECM organisation (Lovell, C., Smolenski, K., Duance, V., Light, N., Young, S., Dyson, M. (1987) *Type I and III collagen content and fibre distribution in normal human skin during ageing*. British Journal of Dermatology, 117, 419-428; and Theochandis, G., Connelly, J. T. (2017) *Minor collagens of the skin with not so minor functions*. J. Anat.). In fact, it has been proven that collagen VI contributes to the appropriate binding and structure of collagen I (Bonaldo, P et. al. (1990) *Structural and Functional Features of the α3 Chain Indicate a Bridging Role for Chicken Collagen VI in Connective Tissues*. Biochemistry, 29, 1245-1254). In addition to their essential structural function, collagens are also involved in cell adhesion, chemotaxis and migration. They dynamically interact with cells, growth factors and cytokines to regulate tissue remodelling in the course of cell growth, differentiation, morphogenesis and wound repair (van der Rest, M., Garrone, R. (1991) *Collagen family of proteins*. FASEB J., 13, 2814-23.; Singer, A. J., Clark, R. A. (1999) *Cutaneous wound healing*. N Engl J Med., 341(10), 738-46; Gelse, K., POschl, E., Aigner, T. (2003) *Collagens-structure, function, and biosynthesis*. Advanced Drug Delivery Reviews, 55(12), 1531-1546; and Ricard-Blum S. (2011). *The collagen family*. Cold Spring Harbor perspectives in biology, 3(1), a004978).

Collagen destruction, along with damage to the other structural components of the skin (this is, elastic and reticular fibres) is thought to underlie the characteristic alterations in the appearance of aged skin (Bailey, A. J. (2001). *Molecular mechanisms of ageing in connective tissue*. Mech Ageing Dev, 122 pp. 735-755; Schwartz, E., Cruickshank, F. A., Perlish, J. S., Fleischmajer, R. (1989) *Alterations in dermal collagen in ultraviolet irradiated hairless mice*. J Invest Dermatol, 93, pp. 142-146; Schwartz, E., Cruickshank, F. A., Christensen, C. C., Perlish, J. S., Lebwohl, M. (1993) *Collagen alterations in chronically sun-damaged human skin*. Photochem Photobiol, 58, pp. 841-844; Smith, J. G., Davidson, E. A., Sams, W. M., Clark, R. D. (1962) *Alterations in human dermal connective tissue with age and chromic sun damage*. J Invest Dermatol, 39, pp. 347-350; Maloney, S. J., Edmonds, S. H., Giddens, L. D., Learn, D. B. (1992) *The hairless mouse model of photoaging: Evaluation of the relationship between dermal elastin, collagen, skin thickness and wrinkles*. Photochem Photobiol, 56, pp. 505-511; Fligiel, S. E. G., Varani, J., Datta, S. C., Kang, S., Fisher, G. J., Voorhees, J. J. (2003) *Collagen Degradation in Aged/Photodamaged Skin in Vivo and after Exposure to Matrix Metalloproteinase—I in Vito*. J. Invest. Dermatol., 120, pp. 842-848; and Marks, R. (Ed.) (1992) Sun-Damaged Skin. Martin Dunitz, London).

Moreover, it has been described that the homeodomain protein Mohawk (Mkx) is abundantly expressed in the skin (Uhlen, M. et al. (2015) Proteomics. *Tissue-based map of the human proteome*. Science 347, 1260419) and said protein has been linked with increased synthesis of collagen and increased collagen fibril formation, as well as appropriate modulation of other genes related with the generation of the extracellular matrix (Nakamichi, R. et. al. (2016) *Mohawk promotes the maintenance and regeneration of the outer annulus fibrous of intervertebral discs*. nature communications, 7:12503; Nakahara, H. (2013) *Transcription Factor Mohawk and the Pthogenesis of Human Anterior Criciate Ligament Degradation*, arthritis & rheumatism, vol. 65, 8, 2081-2089).

In recent years, the number of active ingredients to improve signs of skin aging, such as loss of firmness, skin texture and wrinkling, has increased considerably. Examples of such active ingredients are retinoids, vitamins or botanical extracts (Bradley E. J., Griffiths C. E. M., Sherratt M. J., Bell M. and Watson R. E. B. (2015), *Over-the-counter anti-ageing topical agents and their ability to protect and repair photoaged skin*. Maturitas, 80, 265-272).

In the case of retinoids, noteworthy is retinoic acid which is nowadays the 'gold-standard' for the induction of synthesis of several molecules of the ECM (for example, collagen, fibronectin or laminin; Varani J., Mitra R. S., Gibbs D., Phan S. H., Dixit V. M., Mitra R., Wang T., Siebert K. J., Nickoloff B. J., Voorhees J. J. (1990), *All-Trans Retinoic Acid Stimulates Growth and Extracellular Matrix P(duction in Growth-Inhibited Cultured Human Skin Fibroblasts*. The Journal of Investigative Dermatology, 94, 717-723). Hence, retinoic acid has been considered one of the most powerful compounds to treat the signs of aging, as it can significantly improve the clinical appearance of facial wrinkles by upregulating the transcription and synthesis of proteins of the ECM such as collagen and fibronectin, and the inhibition of matrix metalloproteinases (hereinafter, MMP) (Varani J., Mitra R. S., Gibbs D., Phan S. H., Dixit V. M., Mitra R., Wang T., Siebert K. J., Nickoloff B. J., Voorhees J. J. (1990), *All-Trans Retnoic Acid Stimulates Growth and Extracellular Matrix P(duction in G(owth-Inhibited Cultured Human Skin Fibroblasts*. The Journal of Investigative Dermatology, 94, 717-723). However, there are several drawbacks in the use of retinoic acid as, for example: retinoic acid has to be used cautiously as it can easily produce skin irritation and it is not recommended to combine retinoic acid and sun exposure. Another major concern when using retinoids is their instability, especially in the presence of oxygen and light (Sorg O., Antille C., Kaya G. and Saurat J-H. (2006), *Retinoids in cosmeceuticals*. Dermatologic Therapy, 19, 289-296).

Antioxidants are also used in order to reduce the concentration of free radicals in the skin and, therefore, counteract collagen degradation. An example of said antioxidants is ascorbic acid (also known as Vitamin C). Ascorbic acid, in addition to its antioxidant effect, induces the synthesis of proteins from the ECM (collagen I and III and elastin) while promoting epidermal differentiation and inhibiting Matrix metalloproteinase-1 (MMP1), among others. Unfortunately, ascorbic acid, is extremely unstable and undergoes oxidation especially at high temperatures, aerobic conditions, high pH and/or when exposed to light (Manela-Azulay M., Azulay V., Aguinaga F., Issa M. C. (2017), *Vitamins and other Antioxidants*. Daily Routine in Cosmetic Dermatology, 1-13).

In addition to chemically synthesized compounds, a wide range of botanical extracts and plant derived compounds are found in the market with multiple applications, such as, for example, grape extracts which comprise resveratrol (an antioxidant); green tea which comprises polyphenols; or soy which comprises isoflavones. However, the in vivo efficacy and composition of these ingredients is not sufficiently scientifically validated.

Hyaluronic acid, due to its viscoelastic properties and its capacity to retain water, has also been used in the cosmetic industry to keep skin hydrated, maintain elasticity and treat wrinkles by improving the roughness or even used as a dermal filler. However, currently, hyaluronic acid, is obtained from several sources, such as rooster combs or bacterial extracts and, consequently, these products can contain impurities and need to be characterized thoroughly (Kogan G., Soltés L., Stem R. and Gemeiner P. (2007), *Hyaluronic acid: a natural biopolymer with a broad range of biomedical and industrial applications*. Biotechnological Letters 29, 17-25).

On the other hand, peptides can also be incorporated in cosmetic formulas to improve the signs of skin aging. Bioactive peptides can imitate body's own molecules and influence processes such as collagen synthesis, with the advantage that they have much better tolerability and stability. In addition, a wide range of activities, chemistries and indications can be developed for them (Zhang L. and Falla T. J. (2009), *Cosmeceuticals and peptides*. Clinics in dermatology, 27, 485-494).

Despite the extensive variety of compounds and/or extracts in the field, there is still the need for alternative compositions with novel mechanisms of action which allow the prevention, reduction and/or elimination of the signs of skin aging (chronological and/or environmental aging) and/or provide for skin rejuvenation.

SUMMARY OF THE INVENTION

The inventors of the present invention, after extensive and exhaustive research, have surprisingly found peptides which provide for an increased expression and synthesis of homeodomain protein Mohawk and, as a consequence an increase in expression and synthesis of collagen. In addition, the peptides found by the inventors of the present invention modulate gene expression favouring or upregulating genes in charge of synthesizing and structuring the extracellular matrix, while inhibiting or downregulating genes in charge of degrading said extracellular matrix. The peptides of the present invention also increase collagen synthesis and improve collagen density and thickness in skin explants. Furthermore, their skin smoothing properties, and anti-wrinkle and anti-aging effects, have been demonstrated in vivo. Therefore, the peptides of the present invention show an anti-aging and rejuvenating activity and, hence, solve the problems present in the state of the art and mentioned above.

The inventors are not aware of any prior art which provides for peptides with the above-mentioned mechanisms of action and, hence, the above-mentioned activities.

DETAILED DESCRIPTION OF THE INVENTION

Figure 1:
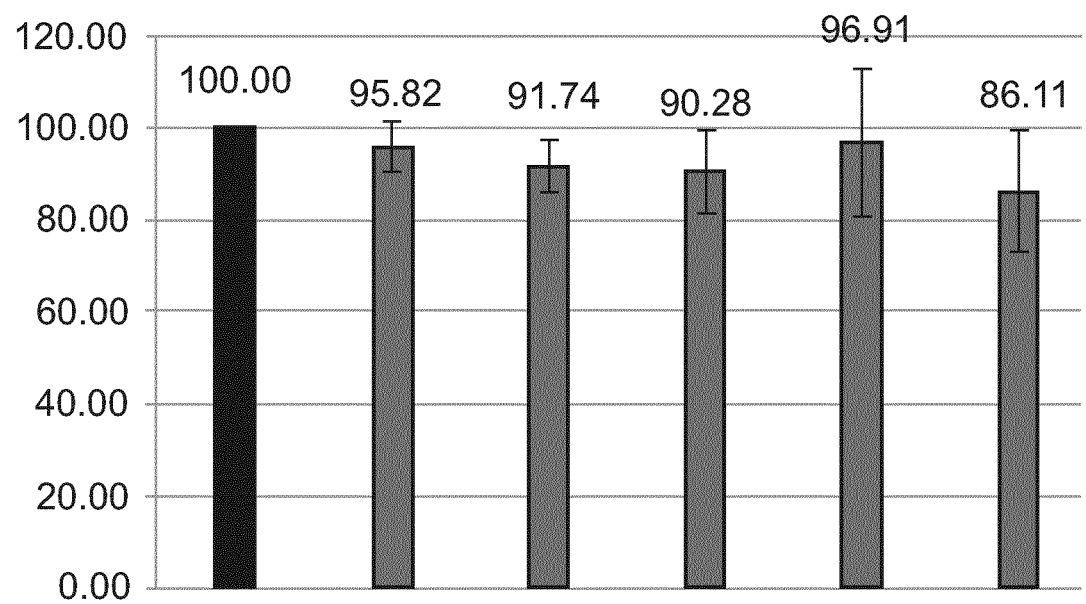
FIG. 1 shows the percentage HEKa cell viability after the treatment with growing concentrations of peptide Pal-SEQ ID NO: 1-$NH_2$ in comparison with the basal state.

In a first aspect, the present invention refers to a peptide capable of increasing the homeodomain protein Mohawk.

In a second aspect, the present invention refers to a composition comprising a peptide of the present invention.

Furthermore, the present invention in a third aspect refers to the use as a cosmetic of a peptide or a composition of the present invention in a subject in need thereof.

In a fourth aspect, the present invention refers to the cosmetic use of a peptide or a composition of the present invention in a subject in need thereof.

In a fifth aspect, the present invention refers to a cosmetic method, characterized in that it comprises the use of a peptide or a composition of the present invention in a subject in need thereof.

The term "non-cyclic aliphatic group" and its plural, as used herein, have the common meaning given in the state of the art to said terms. Therefore, these terms refer to, for example and not restricted to, linear or branched alkyl, alkenyl and alkynyl groups.

The term "alkyl group" and its plural, as used herein, refer to a saturated, linear or branched group, which has between 1 and 24, preferably between 1 and 16, more preferably between 1 and 14, even more preferably between 1 and 12, and even more preferably still between 1, 2, 3, 4, 5 or 6 carbon atoms and which is bound to the rest of the molecule by a simple bond, including, for example and not restricted to, methyl, ethyl, isopropyl, n-propyl, i-propyl, isobutyl, tert-butyl, n-butyl, sec-butyl, n-pentyl, n-hexyl, heptyl, octyl, decyl, dodecyl, lauryl, hexadecyl, octadecyl, amyl, 2-ethylhexyl, 2-methylbutyl, 5-methylhexyl and similar. The alkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alkenyl group" and its plural, as used herein, refer to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the vinyl, oleyl, linoleyl and similar groups. The alkenyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alkynyl group" and its plural, as used herein, refer to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the ethinyl group, 1-propinyl, 2-propinyl, 1-butinyl, 2-butinyl, 3-butinyl, pentinyl, such as 1-pentinyl and similar groups. The alkynyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alicyclic group" and its plural, as used herein, have the common meaning given in the state of the art to said terms. Hence, these terms are used to refer to, for example and not restricted to, cydoalkyl or cycloalkenyl or cycloalkynyl groups.

The term "cycloalkyl" and its plural, as used herein, refer to a saturated mono- or polycyclic aliphatic group which has between 3 and 24, preferably between 3 and 16, more preferably between 3 and 14, even more preferably between 3 and 12, even more preferably still 3, 4, 5 or 6 carbon atoms and which is bound to the rest of the molecule through a single bond, including, for example and not limited to, cyclopropyl, cyclobutyl, cyclopentyl, cyclohexyl, cycloheptyl, methyl cyclohexyl, dimethyl cyclohexyl, octahydroindene, decahydronaphthalene, dodecahydro-phenalene, adamantyl and similar, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "cycloalkenyl" and its plural, as used herein, refer to a non-aromatic mono- or polycyclic aliphatic group which has between 5 and 24, preferably between 5 and 16, more preferably between 5 and 14, even more preferably between 5 and 12, even more preferably still 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the cyclopent-1-en-1-yl group and similar groups, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "cycloalkynyl" and its plural, as used herein, refer to a non-aromatic mono- or polycyclic aliphatic group which has between 8 and 24, preferably between 8 and 16, more preferably between 8 and 14, even more preferably between 8 and 12, even more preferably still 8 or 9 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the cyclooct-2-yn-1-yl group and similar, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "aryl group" and its plural, as used herein, refer to an aromatic group which has between 6 and 30, preferably between 6 and 18, more preferably between 6 and 10, even more preferably 6 or 10 carbon atoms, which comprises 1, 2, 3 or 4 aromatic rings, bound by a carbon-carbon bond or fused, and which is bound to the rest of the molecule through a single bond, including, for example and not restricted to, phenyl, naphthyl, diphenyl, indenyl, phenanthryl or anthranyl among others. The aryl group can be optionally substituted by one or more substituents, such as, halo, hydroxy, alkoxy, carboxy, carbonyl, cyano, acyl, alkoxy-carbonyl, amino, nitro, mercapto and alkoxythio.

The term "aralkyl group" and its plural, as used herein, refer to an alkyl group substituted by an aromatic group, with between 7 and 24 carbon atoms and including, for example and not restricted to, —($CH_2$)1-6-phenyl, —($CH_2$)1-6-(1-naphtyl), —($CH_2$)1-6-(2-naphtyl), —($CH_2$)1-6-CH(phenyl)$_2$ and similar. The aralkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "heterocyclic group" and its plural, as used herein, refer to a 3-10 member heterocycyl or hydrocarbon ring, in which one or more of the ring atoms, preferably 1, 2 or 3 of the ring atoms, is a different element to carbon, such as nitrogen, oxygen or sulfur and may be saturated or unsaturated. For the purposes of this invention, the heterocyclyl can be a cyclic, monocyclic, bicyclic or tricyclic system which may include fused ring systems; and the nitrogen, carbon or sulfur atoms can be optionally oxidized in the heterocyclyl radical; the nitrogen atom can optionally be quatemized; and the heterocyclyl radical may be partially or completely saturated or may be aromatic. With increasing preference, the term heterocyclic relates to a 5 or 6-member ring. The heterocyclic groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "heteroarylalkyl group" and its plural, as used herein, refer to an alkyl group substituted with a substituted or unsubstituted aromatic heterocyclyl group, the alkyl group having from 1 to 6 carbon atoms and the aromatic heterocydyl group between 2 and 24 carbon atoms and from 1 to 3 atoms other than carbon and including, for example and not restricted to, —($CH_2$)1-6-imidazolyl, —($CH_2$)1-6-triazolyl, —($CH_2$)1-6-thienyl, —($CH_2$)1-6-furyl, —($CH_2$)1-6-pyrrolidinyl and similar. The heteroarylalkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The terms "halo" or "halogen", as used in the present document, refer to fluorine, chlorine, bromine or iodine, and its anions are referred to as halides.

As used herein, the term "derivative" and its plural, refer both to cosmetically acceptable compounds, this is, derived from the compound of interest that can be used in the preparation of a cosmetic, and to cosmetically unacceptable derivatives since these may be useful in the preparation of cosmetically acceptable derivatives.

As used in the present document, the term "salt" and its plurals refer to any type of salt from among those known in the state of the art, for example, halide salts, hydroxy acid salts (such as oxyacid salts, acid salts, basic salts and double salts), hydroxo salts, mixed salts, oxy salts or other hydrated salts. This term comprises both cosmetically and cosmetically unacceptable salts, since the latter may be useful in the preparation of cosmetically acceptable salts.

As used in the present document, the term "isomer" and its plural refer to optical isomers, enantiomers, stereoisomers or diastereoisomers. The individual enantiomers or diastereoisomers, as well as their mixtures, may be separated by conventional techniques known in the state of the art.

As used herein, the term "solvate" and its plural refer to any solvate known in the state of the art, such as polar, apolar or amphiphilic solvates, and include any cosmetically acceptable solvate which, when administered or applied to the interested subject (directly or indirectly) provides the compound of interest (the peptide or peptides of the present invention). Preferably, the solvate is a hydrate, a solvate with an alcohol such as methanol, ethanol, propanol or isopropanol, a solvate with an ester such as ethyl acetate, a solvate with an ether such as methyl ether, ethyl ether or TH F (tetrahydrofuran) or a solvate with DMF (dimethylformamide), and more preferably a hydrate or a solvate with an alcohol such as ethanol.

In addition, as used herein, the term "amino add" and its plural indude the amino acids codified by the genetic code as well as uncodified amino acids, whether they are natural or not and whether they are D- and L-amino acids. Examples of uncodified amino acids are, without restriction, citrulline, omithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4 aminobenzoic acid, 4-chlorophenylalanine, 2,3-diaminopropionic acid, 2,4 diaminobutyric acid, cycloserine, camitine, cysteine, penicillamine, pyroglutamic acid, thienylalanine, hydroxyproline, allo-isoleucine, allo-threonine, isonipecotic acid, isoserine, phenylglycine, statin, β-alanine, norleucine, N-methylamino acids, α-amino acids and β-amino acids, among others, as well as their derivatives. Nevertheless, further unnatural amino acids are known in the state of the art (see, for example, "*Unusual amino acids in peptide synthesis*" by D. C. Roberts and F. Vellaccio, The Peptides, Vol. 5 (1983), Chapter VI, Gross E. and Meienhofer J., Eds., Academic Press, New York, USA).

The "percentage of identity" regarding peptides, polypeptides and proteins, as used herein, has the meaning commonly attributed in the state of the art and, hence, relates to the percentage of amino acids which are identical between two amino acid sequences which are compared after an optimal alignment of these sequences, where said percentage is merely statistical and the differences between the two amino acid sequences are randomly distributed throughout the sequence. "Optimal alignment" is understood as that alignment of amino acid sequences giving rise to a greater percentage of identity. The percentage of identity is calculated by determining the number of identical positions in which an amino acid is identical in the two compared sequences, dividing the number of identical positions by the number of compared positions and multiplying the result obtained by 100 to obtain the percentage of identity between the two sequences. The sequence comparisons between two amino acid sequences can be carried out manually or by means of computer programs known in the state of the art, such as the BLAST (Basic Local Alignment Search Tool) algorithm.

As used herein, "homeodomain protein Mohawk", "Mohawk" and "Mkx" are equivalent, are used interchangeably and refer to the protein known as homeodomain protein Mohawk, unless expressly noted otherwise.

As stated previously, in a first aspect, the present invention refers to a peptide capable of increasing Mohawk (hereinafter, Mkx), its acceptable isomers, salts, solvates and/or derivatives and/or mixtures thereof.

Mohawk is increased in a subject to which the peptide is applied. More preferably, in a mammal, even more preferably a human.

Preferably, the increase of Mohawk is an increase in gene expression and protein synthesis of Mohawk.

It is contemplated that the amino acids used or present in the peptides of the present invention are L-amino acids, D-amino acids or combinations thereof. In a preferred embodiment, the amino acids used or present in the peptides of the present invention are L-amino acids.

Preferably, the isomers mentioned above are stereoisomers. It is contemplated that said stereoisomers are enantiomers or diastereoisomers. Hence, in a preferred embodiment of the present invention, the peptide is a racemic mixture, a diastereomeric mixture, a pure enantiomer or a pure diastereoisomer.

Preferably, the peptide of the present invention comprises between 2 and 50 amino acids, more preferably, between 4 and 10 amino acids, more preferably, between 4 and 6 amino acids, even more preferably, 4 amino acids.

It is contemplated that the peptide of the present invention comprises at least one moiety bound at its N-terminus and/or at its C-terminus. Said at least one moiety may be bound to the peptide by any means known in the state of the art, preferably covalently. In a preferred embodiment, the peptide comprises one moiety bound covalently to its N-terminus and one moiety bound covalently to its C-terminus.

In an embodiment, the at least one N-terminus moiety (preferably, one N-terminus moiety) is selected from H, substituted or unsubstituted non-cyclic aliphatic, substituted or unsubstituted alicyclyl, substituted or unsubstituted heterocydyl, substituted or unsubstituted heteroarylalkyl, substituted or unsubstituted aryl, substituted or unsubstituted aralkyl and $R_5$—CO—, wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms. Even more preferably, the at least one N-terminus moiety (preferably, one N-terminus moiety) is selected from Acetyl (hereinafter, Ac) or Palmitoyl (hereinafter, Pal). In the most preferred embodiment, the at least one N-terminus moiety (preferably, one N-terminus moiety) is Pal.

In an embodiment, the at least one C-terminus moiety (preferably, one C-terminus moiety) is selected from is selected from H, —$NR_3R_4$—, —$OR_3$ and —$SR_3$, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl. Even more preferably, the at least one C-terminus moiety (preferably, one C-terminus moiety) is selected from H or $NH_2$. In the most preferred embodiment, the at least one C-terminus moiety (preferably, one C-terminus moiety) is $NH_2$.

Therefore, more preferably, the peptide of the present invention comprises one moiety bound to the N-terminus and one moiety bound to the C-terminus, wherein the moiety bound to the N-terminus is Pal and the moiety bound to the C-terminus is $NH_2$.

In a preferred embodiment, the sequence of a peptide of the present invention is in accordance with formula (I):

$$R_1\text{-}AA_1\text{-}AArAA_3\text{-}AA_4\text{-}R_2 \qquad (I)$$

its cosmetically acceptable isomers, salts, solvates and/or derivatives and mixtures thereof, wherein:

$AA_1$ is His;

$AA_2$ is selected from the group of amino acids with an aromatic side-chain;

$AA_3$ is selected from Lys or Arg;

$AA_4$ is selected from the group of amino acids with an aliphatic non-polar side-chain.

$R_1$ is selected from H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms; and $R_2$ is selected from H, —$NR_3R_4$—, —$OR_3$ and —$SR_3$, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl.

As stated above, it is contemplated that the amino acids used or present in the peptides of the present invention are L-amino acids, D-amino acids or combinations thereof. In a preferred embodiment, the amino acids used or present in the peptides of the present invention are L-amino acids.

Also as stated above, preferably, the isomers mentioned above are stereoisomers. It is contemplated that said stereoisomers are enantiomers or diastereoisomers. Hence, in a preferred embodiment of the present invention, the peptide is a racemic mixture, a diastereomeric mixture, a pure enantiomer or a pure diastereoisomer.

$R_1$ is, preferably, selected from Pal or Ac, even more preferably, $R_1$ is Pal.

Preferably, $R_2$ is selected from H or $NH_2$, even more preferably, $R_2$ is $NH_2$.

Hence, more preferably, $R_1$ is Pal and $R_2$ is $NH_2$.

Preferably, in formula (I) $AA_2$ is selected from the group of Phe, Tyr and Trp, more preferably $AA_2$ is Tyr.

Preferably, in formula (I) $AA_3$ is Arg.

Also preferably, in formula (I) $AA_4$ is selected from the group of Ala, Val, Leu and Ile, more preferably $AA_4$ is Ala.

Therefore, in a preferred embodiment, in formula (I):
$AA_1$ is His;
$AA_2$ is selected from the group of Phe, Tyr and Trp;
$AA_3$ is selected from Lys or Arg;
$AA_4$ is selected from the group of Ala, Val, Leu and Ile;
more preferably, in formula (I):
$AA_1$ is His;
$AA_2$ is selected from the group of Phe, Tyr and Trp;
$AA_3$ is Arg;
$AA_4$ is selected from the group of Ala, Val, Leu and Ile.

Even more preferably, the sequence of the peptide in accordance with the present invention (this is, the peptide of formula (I)) is:

$R_1$-His-Tyr-Arg-Ala-$R_2$($R_1$-SEQ ID NO: 1-$R_2$);

In the most preferred embodiment, the sequence of the peptide of the present invention (this is, in accordance with formula (I)) is:

Pal-His-Tyr-Arg-Ala-$NH_2$(Pal-SEQ ID NO: 1-$NH_2$);

The peptides of the present invention may be synthesized and produced by any means known in the state of the art. For example, they may be synthesized and produced by chemical synthesis (preferably, by means of solid phase peptide synthesis), expressing said peptides in cell cultures or by means of transgenic production of the peptide in plants or animals. In addition, the peptides of the present invention may be purified by any means known in the state of the art.

As it is apparent from the examples included below, the peptides of the present invention, provide for increased expression and synthesis of Mohawk as well as of collagen VI. In addition, they modulate gene expression favouring or upregulating genes in charge of synthesizing and structuring the extracellular matrix, while inhibiting or downregulating genes in charge of degrading said extracellular matrix. The peptides of the present invention also increase collagen synthesis and improve collagen density and thickness in skin explants. Moreover, they have skin smoothing, antiwrinkle, and anti-aging effects when topically applied to the face of female subjects.

Therefore, the peptides of the present invention solve the above-mentioned problems and provide for additional or alternative peptides with cosmetic activities (for example, anti-aging and rejuvenating activity), that are able to improve signs of the skin related with aging as, for example, wrinkles, roughness and/or sagginess; or provide for skin rejuvenation and/or improvement of skin imperfections as, for example, body firming, body sculpting, facial repositioning, skin tightening and/or pore refining.

Also, within the scope of the present invention are peptides which incorporate conservative amino acid substitutions with regard to any of the peptides of the present invention as described above and which still show the activities described herein for the peptides of the present invention.

In addition, also included within the scope of the present invention are peptides with a 70% percentage identity, preferably 80%, more preferably 90%, more preferably 95%, even more preferably 99% percentage identity with the peptide Ri-His-Tyr-Arg-Ala-$R_2$ ($R_1$-SEQ ID NO: 1-$R_2$), preferably, Pal-His-Tyr-Arg-Ala-$NH_2$ (Pal-SEQ ID NO: 1-$NH_2$) and which still show the activities described herein for the peptides of the present invention.

In the most preferred embodiment, the composition of the present invention is suited or adapted to be applied topically, more preferably, in the face and/or the body of a subject, more preferably, in the face, neck, hands, arms, legs, breasts and/or buttocks of a subject, even more preferably in the face and/or neck of a subject (preferably, a human).

In a second aspect, the present invention refers to a composition comprising at least one peptide in accordance with the present invention.

It is contemplated that the composition of the present invention comprises one type of peptide of the present invention or a combination or mixture of different peptides of the present invention, preferably, one type of peptide of the present invention.

In a preferred embodiment, the composition of the present invention is a cosmetic composition.

The composition of the present invention comprises a cosmetically effective amount of the at least one peptide of the present invention. More preferably, the composition of the present invention comprises from 0.0001% (mass/volume in g/100 mL, hereinafter, m/v) to 0.05% (m/v) of at least one peptide of the present invention. In a most preferred embodiment, the composition of the present invention comprises from 0.0001% (m/v) to 0.001% (m/v) of at least one peptide of the present invention, more preferably, 0.0005% (m/v). In another most preferred embodiment, the composition of the present invention comprises from 0.05% (m/v) to 0.001% (m/v) of at least one peptide of the present.

The composition of the present invention, as a consequence of the activity of the peptides of the present invention, provides for the improvement of signs of the skin related with aging as, for example, wrinkles, roughness and/or sagginess; or provides for skin rejuvenation and/or improvement of skin imperfections as, for example, body firming, body sculpting, facial repositioning, skin tightening and/or pore refining.

It is contemplated that the composition of the present invention also comprises at least one additional cosmetic ingredient. Said additional cosmetic ingredient can be at least one excipient and/or at least one additional cosmetic active ingredient.

The additional cosmetic ingredients comprise those usually used in the state of the art as, for example, adjuvants such as stabilizer, solubilizer, vitamin, colorant and perfumery; carriers; and/or other cosmetic active ingredients.

Said additional cosmetic ingredients, must be physically and chemically compatible with the rest of the components of the composition and, especially, with the peptides of the present invention comprised in the composition of the present invention. Likewise, the nature of said additional cosmetic ingredients must not unacceptably alter the benefits of the peptides and compositions of the present invention. Said additional cosmetic ingredients may be of a synthetic or natural origin, such as, for example, plant extracts, or they can be derived from a biofermentation process (see, for example, CTFA Cosmetic Ingredient Handbook, Eleventh Edition (2006)).

It is contemplated that the additional cosmetic ingredients mentioned above comprise those ingredients commonly used in compositions for caring for, cleaning skin and/or hair, and/or deodorants and/or creams to prevent hyperhidrosis; such as, for example, agents inhibiting melanin synthesis, whitening or depigmenting agents, anti-aging agents, agents inhibiting NO-synthase, antioxidants, anti-atmospheric pollution and/or free radical trapping agents, anti-glycation agents, emulsifying agents, emollients, organic solvents, liquid propellants, skin conditioners such as for example wetting agents, moisture retaining substances, alpha hydroxy acids, moisturizers, vitamins, pigments or colorants, dyes, gelling polymers, thickeners, surfactants, softeners, other anti-wrinkle agents, agents capable of reducing or eliminating bags under the eyes, exfoliating agents, antimicrobial agents, antifungal agents, bactericides, agents stimulating dermal or epidermal macromolecule synthesis and/or capable of preventing or inhibiting their degradation, such as for example agents stimulating collagens synthesis, agents stimulating elastin synthesis, agents stimulating laminin synthesis, agents inhibiting collagen degradation, agents inhibiting elastin degradation, agents stimulating fibroblast proliferation, agents stimulating keratinocyte proliferation, agents stimulating keratinocyte differentiation, agents stimulating lipid synthesis and synthesis of components of the stratum corneum (ceramides, fatty acids, etc.), dermorelaxing agents, agents stimulating glycosaminoglycan synthesis, DNA repairing agents, DNA protecting agents, agents stimulating proteosome activity, anti-pruritus agents, agents for treating sensitive skin, reaffirming agents, astringent agents, sebum production regulating agents, agents stimulating lipolysis, anti-cellulite agents, calming agents, anti-inflammatory agents, agents acting on capillary circulation and/or microcirculation, agents acting on cell mitochondria, agents intended to improve the dermo-epidermal junction, preservatives, perfumes, chelating agents, plant extracts, essential oils, marine extracts, agents derived from a biofermentation process, mineral salts, cell extracts and/or solar filters (organic or mineral photoprotective agents active against ultraviolet A and B rays) among others.

In an embodiment, at least one of the additional cosmetic ingredients is a cosmetic active principle or substance which may exert the same, similar, complementary or different cosmetic activities as those disclosed above for the peptides of the present invention. It is contemplated that the composition of the present invention comprises other anti-wrinkling or anti-aging agents, for example, collagen, elastin, growth factors, hyaluronic acid boosters, barrier function agents, illuminating agents, agents stimulating the expression and/or synthesis of collagen I, III, IV and/or VI and laminin; agents stimulating the synthesis of glycosaminoglycans or hyaluronic acid; agents stimulating the expression and/or synthesis of elastin and other elastic fibres-related proteins; agents inhibiting collagen and/or elastic fibres degradation; agents stimulating the expression and/or synthesis of mitochondria-related proteins (for example, sirtuins and aconitase); agents stimulating the expression and/or synthesis of focal adhesion proteins; agents stimulating keratinocytes and/or fibroblasts proliferation and/or differentiation; antioxidants; anti-atmospheric pollution and/or free radical trapping agents; anti-glycation agents; detoxifying agents; agents decreasing chronological aging, environmental aging and inflammation aging; and agents decreasing melanin production and/or inhibiting tyrosinase and/or agents stimulating lipid synthesis and synthesis of components of the epidermis (keratins) and more specifically the stratum corneum (keratins, ceramides, filaggrin, loricrin and SPRR1B). More preferably, the at least one of the additional cosmetic ingredients is Argireline® (Acetyl Hexapeptide-8), Leuphasyl™ (Pentapeptide-3), Inyline® (Acetyl Hexapeptide-30), Syn-Ake® (Tripeptide-3) or combinations thereof.

In addition, the composition of the present invention (or the peptide of the present invention) can be formulated in any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the composition of the present invention or a peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposheres, millicapsules, microcapsules and nanocapsules, as well as in microemulsions and nanoemulsions, for the purpose of obtaining greater penetration of the active ingredient.

In a preferred embodiment, the composition of the present invention is suited or adapted to be applied by means of iontophoresis, more preferably, in the face and/or the body of a subject, more preferably, in the face, neck, hands, arms, legs, breasts and/or buttocks of a subject, even more preferably in the face and/or neck of a subject (preferably, a human).

In the most preferred embodiment, the composition of the present invention is suited or adapted to be applied topically (more preferably, in the form of a cream), more preferably, in the face and/or the body of a subject, more preferably, in the face, neck, hands, arms, legs, breasts and/or buttocks of a subject, even more preferably in the face and/or neck of a subject (preferably, a human).

As already stated above, in a third aspect, the present invention refers to the use as a cosmetic of a peptide or a composition of the present invention in a subject in need thereof.

As noted above, preferably, the composition of the present invention is a cosmetic composition.

In a preferred embodiment, the use as a cosmetic is to reduce, prevent and/or eliminate signs of skin aging.

As it is evident, the signs of skin aging mentioned above are cosmetic signs of skin aging.

Skin aging is due to chronological and/or environmental aging.

The cosmetic signs of skin aging are, preferably, wrinkles, roughness and/or sagginess, more preferably, facial wrinkles, facial sagginess and/or facial roughness, even more preferably, facial wrinkles.

In another preferred embodiment, the use as a cosmetic is for skin rejuvenation and/or to reduce, prevent and/or eliminate skin imperfections, more preferably, for skin firming, body sculpturing, facial repositioning, skin tightening and/or pore refining, more preferably, body firming, body sculpturing, facial repositioning, facial skin tightening and/or facial pore refining, even more preferably, facial repositioning and/or facial skin tightening.

Body firming and/or body sculpturing, preferably, refer to buttock, breast, arm and/or leg firming and/or sculpturing.

Therefore, the peptides and compositions of the present invention can also be used to treat the loss of firmness or tightness of the skin, preferably loss of tightness of the skin, even more preferably loss of tightness of facial skin.

As noted above, the peptides of the present invention can also be used for the treatment of the loss of organized collagen fibres and, hence, preferably, for the treatment of facial repositioning. This treatment of the loss of organized collagen fibres, as derived directly from the examples below, is performed, at least, improving the production of homeodomain protein Mohawk and Collagen VI.

Also, in a preferred embodiment, the subject is a mammal, even more preferably, a human.

In a preferred embodiment, the peptide or the composition of the present invention is applied by means of iontophoresis, more preferably, in the face and/or the body of the subject, more preferably, in the face, neck, hands, arms, legs, breasts and/or buttocks of the subject, even more preferably in the face and/or neck of the subject (preferably, a human).

In the most preferred embodiment, the peptide or the composition of the present invention is applied topically (more preferably in the form of a cream), more preferably, in the face and/or the body of the subject, more preferably, in the face, neck, hands, arms, legs, breasts and/or buttocks of the subject, even more preferably in the face and/or neck of the subject (preferably, a human).

In addition, in the use as a cosmetic of the present invention, the peptide or the composition of the present invention are used in a cosmetically effective amount. More preferably, the peptide of the present invention is used at a concentration of 0.0001% (m/v) to 0.05% (m/v). In a most preferred embodiment, the peptide of the present invention is used at a concentration of 0.0001% (m/v) to 0.001% (m/v), more preferably, 0.0005% (m/v). In another most preferred embodiment, the peptide of the present invention is used at a concentration of 0.05% (m/v) to 0.001% (m/v).

It is contemplated that the composition of the present invention, as already stated above, also comprises at least one additional cosmetic ingredient Said additional cosmetic ingredient can be at least one excipient and/or at least one additional cosmetic active ingredient, which can be as explained above. It is also contemplated that the peptide of the present invention is used in combination with at least one additional cosmetic ingredient which is in accordance with what has been stated above.

In addition, the peptide of the present invention and the composition of the present invention can be formulated in any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The peptide and the composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the composition of the present invention or a peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposphere, millicapsules, microcapsules and nanocapsules, as well as in microemulsions and nanoemulsions, for the purpose of obtaining greater penetration of the active ingredient.

In a fourth aspect, the present invention refers to the cosmetic use of a peptide or a composition of the present invention (this is, as explained above) in a subject in need thereof.

As noted above, preferably, the composition of the present invention is a cosmetic composition.

In a preferred embodiment, the cosmetic use is to reduce, prevent and/or eliminate signs of skin aging.

As it is evident, the signs of skin aging mentioned above are cosmetic signs of skin aging.

Skin aging is due to chronological and/or environmental aging.

The cosmetic signs of skin aging are, preferably, wrinkles, roughness and/or sagginess, more preferably, facial wrinkles, facial sagginess and/or facial roughness, even more preferably, facial wrinkles.

In another preferred embodiment, the cosmetic use is for skin rejuvenation and/or to reduce, prevent and/or eliminate skin imperfections, more preferably, for skin firming, body sculpturing, facial repositioning, skin tightening and/or pore refining, more preferably, body firming, body sculpturing, facial repositioning, facial skin tightening and/or facial pore refining, even more preferably, facial repositioning and/or facial skin tightening.

Body firming and/or body sculpturing, preferably, refer to buttock, breast, arm and/or leg firming and/or sculpturing.

Therefore, the peptides and compositions of the present invention can also be used to treat the loss of firmness or tightness of the skin, preferably loss of tightness of the skin, even more preferably loss of tightness of facial skin.

As noted above, the peptides of the present invention can also be used for the treatment of the loss of organized collagen fibres and, hence, preferably, for the treatment of facial repositioning. This treatment of the loss of organized collagen fibres, as derived directly from the examples below, is performed, at least, improving the production of homeodomain protein Mohawk and Collagen VI.

Also, in a preferred embodiment, the subject is a mammal, even more preferably, a human.

In a preferred embodiment, the peptide or the composition of the present invention is applied by means of iontophoresis, more preferably, in the face and/or the body of the subject, more preferably, in the face, neck, hands, legs, arms, breasts and/or buttocks of the subject, even more preferably in the face and/or neck of the subject.

In the most embodiment, the peptide or the composition of the present invention is applied topically (more preferably in the form of a cream), more preferably, in the face and/or the body of the subject, more preferably, in the face, neck, hands, arms, legs, breasts and/or buttocks of the subject, even more preferably in the face and/or neck of the subject (preferably, a human).

In addition, in the cosmetic use of the present invention, the peptide or the composition of the present invention are used in a cosmetically effective amount More preferably, the peptide of the present invention is used at a concentration of 0.0001% (m/v) to 0.05% (m/v), more preferably. In a most preferred embodiment, the peptide of the present invention is used at a concentration of 0.0001% (m/v) to 0.001% (m/v), more preferably, 0.0005% (m/v). In another most preferred embodiment, the peptide of the present invention is used at a concentration of 0.05% (m/v) to 0.001% (m/v).

It is contemplated that the composition of the present invention, as already stated above, also comprises at least one additional cosmetic ingredient. Said additional cosmetic ingredient can be at least one excipient and/or at least one additional cosmetic active ingredient, which can be as explained above. It is also contemplated that the peptide of the present invention is used in combination with at least one additional cosmetic ingredient which is in accordance with what has been stated above.

In addition, the peptide of the present invention and the composition of the present invention can be formulated in any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The peptide and the composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the composition of the present invention or a peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposheres, millicapsules, microcapsules and nanocapsules, as well as in microemulsions and nanoemulsions, for the purpose of obtaining greater penetration of the active ingredient.

As stated above, in a fifth aspect, the present invention refers to a cosmetic method characterized in that it comprises the use of a peptide or a composition in accordance with the present invention in a subject in need thereof.

As noted above, preferably, the composition of the present invention is a cosmetic composition.

As it is derivable from the above, the use of the peptide or the composition in accordance with the present invention in the cosmetic method of the present invention is a use as a cosmetic.

In a preferred embodiment, the cosmetic method is to reduce, prevent and/or eliminate signs of skin aging in a subject in need thereof.

As it is evident, the signs of skin aging mentioned above are cosmetic signs of skin aging.

Skin aging is due to chronological and/or environmental aging.

The cosmetic signs of skin aging are, preferably, wrinkles, roughness and/or sagginess, more preferably, facial wrinkles, facial sagginess and/or facial roughness, even more preferably, facial wrinkles.

In another preferred embodiment, the cosmetic method is for skin rejuvenation and/or to reduce, prevent and/or eliminate skin imperfections in a subject in need thereof, more preferably, for skin firming, body sculpturing, facial repositioning, skin tightening and/or pore refining, more preferably, body firming, body sculpturing, facial repositioning, facial skin tightening and/or facial pore refining, even more preferably, facial repositioning and/or facial skin tightening.

Body firming and/or body sculpturing, preferably, refer to buttock, breast, arm and/or leg firming and/or sculpturing.

Therefore, the peptides and compositions of the present invention can also be used to treat the loss of firmness or tightness of the skin, preferably loss of tightness of the skin, even more preferably loss of tightness of facial skin.

As noted above, the peptides of the present invention can also be used for the treatment of the loss of organized collagen fibres and, hence, preferably, for the treatment of facial repositioning. This treatment of the loss of organized collagen fibres, as derived directly from the examples below, is performed, at least, improving the production of homeodomain protein Mohawk and Collagen VI.

Also, in a preferred embodiment, the subject is a mammal, even more preferably, a human.

In a preferred embodiment, the peptide or the composition of the present invention is applied by means of iontophoresis, more preferably, in the face and/or the body of the subject, more preferably, in the face, neck, hands, arms, legs, breasts and/or buttocks of the subject, even more preferably in the face and/or neck of the subject (preferably, a human).

In the most preferred embodiment, the peptide or the composition of the present invention is applied topically (more preferably in the form of a cream), more preferably, in the face and/or the body of the subject, more preferably, in the face, neck, hands, arms, legs, breasts and/or buttocks of the subject, even more preferably in the face and/or neck of the subject (preferably, a human).

Preferably, the subject is a mammal, even more preferably a human.

In addition, in the cosmetic method of the present invention, the peptide or the composition of the present invention are used in a cosmetically effective amount. More preferably, the peptide of the present invention is used at a concentration of 0.0001% (m/v) to 0.05% (m/v). In a most preferred embodiment, the peptide of the present invention is used at a concentration of 0.0001% (m/v) to 0.001% (m/v), more preferably, 0.0005% (m/v). In another most preferred embodiment, the peptide of the present invention is used at a concentration of 0.05% (m/v) to 0.001% (m/v).

It is contemplated that the composition of the present invention, as already stated above, also comprises at least one additional cosmetic ingredient. Said additional cosmetic ingredient can be at least one excipient and/or at least one additional cosmetic active ingredient, which can be as explained above. It is also contemplated that the peptide of the present invention is used in combination with at least one additional cosmetic ingredient which is in accordance with what has been stated above.

In addition, the peptide of the present invention and the composition of the present invention can be formulated in any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The peptide and the composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the composition of the present invention or a peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposomes, millicapsules, microcapsules and nanocapsules, as well as in microemulsions and nanoemulsions, for the purpose of obtaining greater penetration of the active ingredient.

To allow a better understanding, the present invention is described in more detail below with reference to the enclosed drawings, which are presented by way of example, and with reference to illustrative and non-limitative examples.

FIG. 1 shows the percentage HEKa cell viability after the treatment with growing concentrations of peptide Pal-SEQ ID NO: 1-NH$_2$ in comparison with the basal state (this is, stablishing the cell viability of the basal state as 100% and then performing the comparison with the rest of the samples tested). For FIG. 1 columns from left to right in the x-axis correspond to: basal state (cells without treatment) and cells treated with 0.001 mg/mL, 0.005 mg/mL, 0.01 mg/mL, 0.05 mg/mL and 0.1 mg/mL of peptide Pal-SEQ ID NO: 1-NH$_2$, respectively. The y axis shows the percentage of cell viability (with regard to the basal state).

Figure 2:
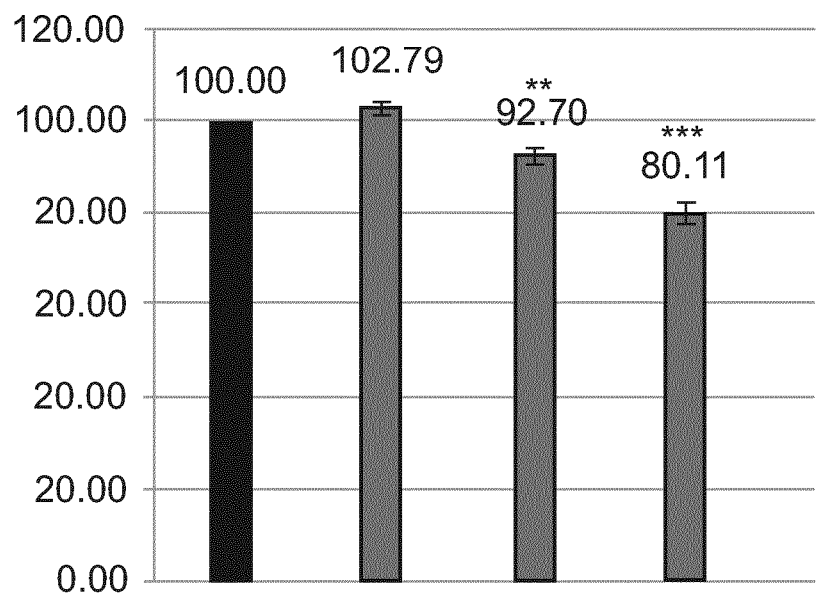
FIG. 2 shows the percentage HDFa cell viability after treatment with peptide Pal-SEQ ID NO: 1-$NH_2$ in comparison with the basal state.

FIG. 2 shows the percentage HDFa cell viability after treatment with peptide Pal-SEQ ID NO: 1-NH$_2$ in comparison with the basal state (this is, stablishing the cell viability of the basal state as 100% and then performing the comparison with the rest of the samples tested). For FIG. 2 columns from left to right in the x-axis correspond to: basal state (cells without treatment) and cells treated with 0.001 mg/mL, 0.005 mg/mL and 0.01 mg/mL of peptide Pal-SEQ ID NO: 1-NH$_2$, respectively. The y axis shows the percentage of cell viability (with regard to the basal state).  refers to a $p<0.01$; and * refers to a $p<0.001$.

Figure 3:
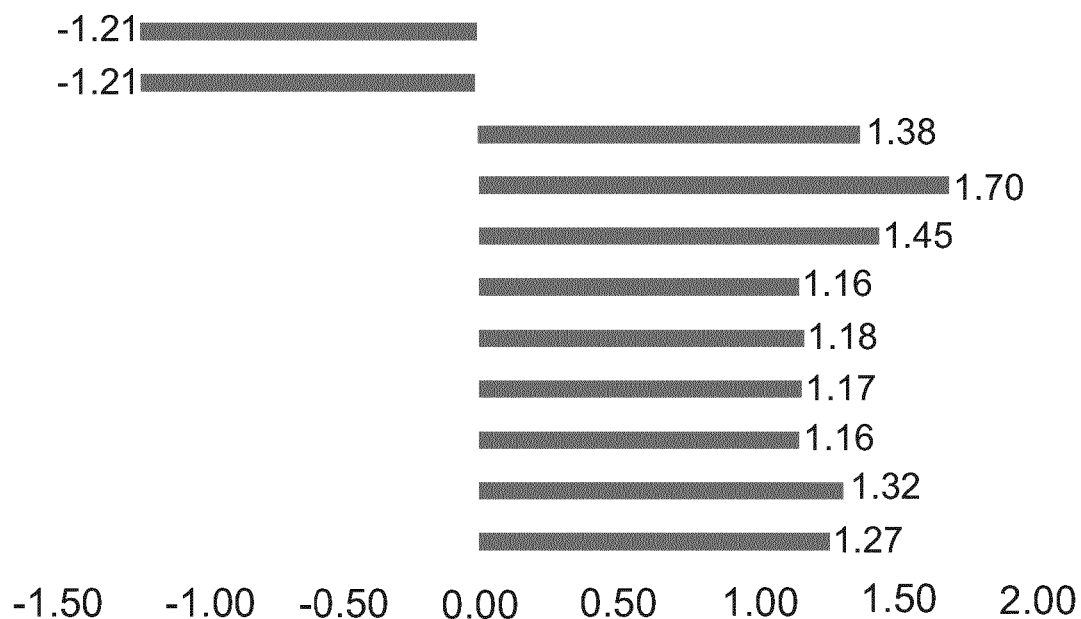
FIG. 3 shows the modulation in gene expression profile in primary human dermal fibroblasts induced by the treatment with peptide Pal-SEQ ID NO: 1-$NH_2$ with regard to untreated primary human dermal fibroblasts and normalized by means of the housekeeping gene GAPDH (Glyceraldehyde 3-phosphate dehydrogenase).

FIG. 3 shows the modulation in gene expression profile in primary human dermal fibroblasts induced by the treatment with peptide Pal-SEQ ID NO: 1-NH$_2$ with regard to untreated primary human dermal fibroblasts and normalized by means of the housekeeping gene GAPDH (Glyceraldehyde 3-phosphate dehydrogenase). FIG. 3 shows the results obtained for the treatment with the above-mentioned peptide (at a concentration of 0.005 mg/mL, during 6 hours for all genes), wherein bars, from top to bottom refer to the following genes: MMP3 (Matrix metalloproteinase-3), MMP1 (Matrix metalloproteinase-1), COL14A1 (Collagen Type XIV Alpha 1 Chain), COL12A1 (Collagen Type XII Alpha 1 Chain), COL7A1 (Collagen Type VII Alpha 1 Chain), COL6A1 (Collagen Type VI Alpha 1 Chain), COL5A1 (Collagen Type V Alpha 1 Chain), COL4A5 (Collagen Type IV Alpha 5 Chain), COL3A1 (Collagen Type III Alpha 1 Chain), MKX (Mohawk homeobox) and ZEB2 (Zinc Finger E-Box Binding Homeobox 2), respectively. The x-axis refers to the fold change with regard to the basal state. A negative fold change refers to downregulation of gene expression while a positive fold change refers to upregulation.

Figure 4:
FIG. 4 shows the modulation in gene expression profile in primary human dermal fibroblasts induced by the treatment with peptide Pal-SEQ ID NO: 1-$NH_2$ with regard to untreated primary human dermal fibroblasts and normalized by means of the housekeeping gene GAPDH (Glyceraldehyde 3-phosphate dehydrogenase).

FIG. 4 shows the modulation in gene expression profile in primary human dermal fibroblasts induced by the treatment with peptide Pal-SEQ ID NO: 1-NH$_2$ with regard to untreated primary human dermal fibroblasts and normalized by means of the housekeeping gene GAPDH (Glyceraldehyde 3-phosphate dehydrogenase). FIG. 4 shows the results obtained for the treatment with the above-mentioned peptide (at a concentration of 0.005 mg/mL, during 24 hours), wherein the bar corresponds to the gene: COL13A1 (Collagen Type XIII Alpha 1 Chain). The x-axis refers to the fold change with regard to the basal state. A negative fold change refers to downregulation of gene expression while a positive fold change refers to upregulation.

Figure 5:
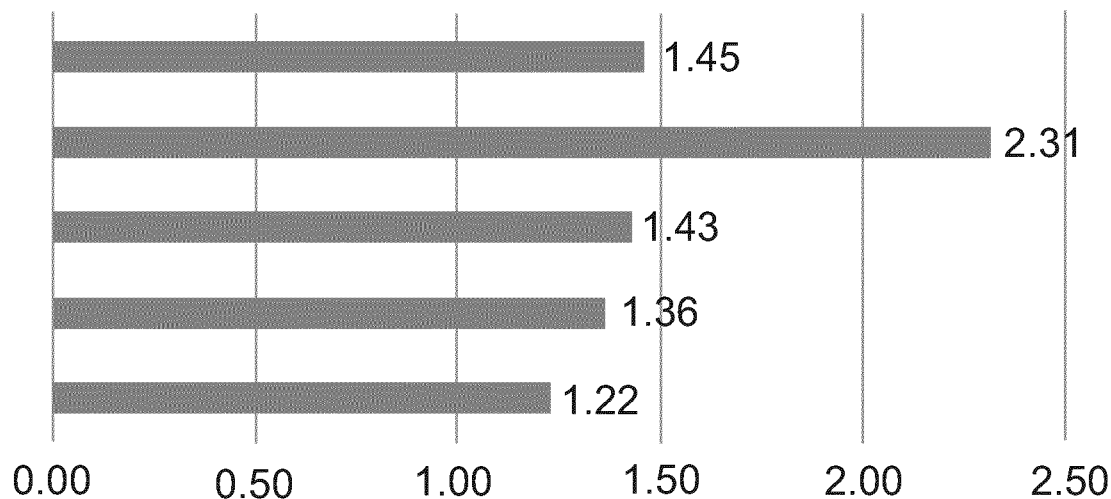
FIG. 5 shows the modulation in gene expression profile in primary human dermal fibroblasts induced by the treatment with peptide Pal-SEQ ID NO: 1-$NH_2$ with regard to untreated primary human dermal fibroblasts and normalized by means of the housekeeping gene GAPDH (Glyceraldehyde 3-phosphate dehydrogenase).

FIG. 5 shows the modulation in gene expression profile in primary human dermal fibroblasts induced by the treatment with peptide Pal-SEQ ID NO: 1-NH$_2$ with regard to untreated primary human dermal fibroblasts and normalized by means of the housekeeping gene GAPDH (Glyceraldehyde 3-phosphate dehydrogenase). FIG. 5 shows the results obtained for the treatment with the above-mentioned peptide (at a concentration of 0.005 mg/mL, during 6 hours for all genes), wherein bars, from top to bottom refer to the following genes: TGFB1 (Transforming growth factor beta-1), FN1 (Fibronectin 1), LOXL3 (Lysyl oxidase like 3), LOXL2 (Lysyl oxidase like 2) and HSP47 (Serpin H1), respectively. The x-axis refers to the fold change with regard to the basal state. A negative fold change refers to downregulation of gene expression while a positive fold change refers to upregulation.

Figure 6:
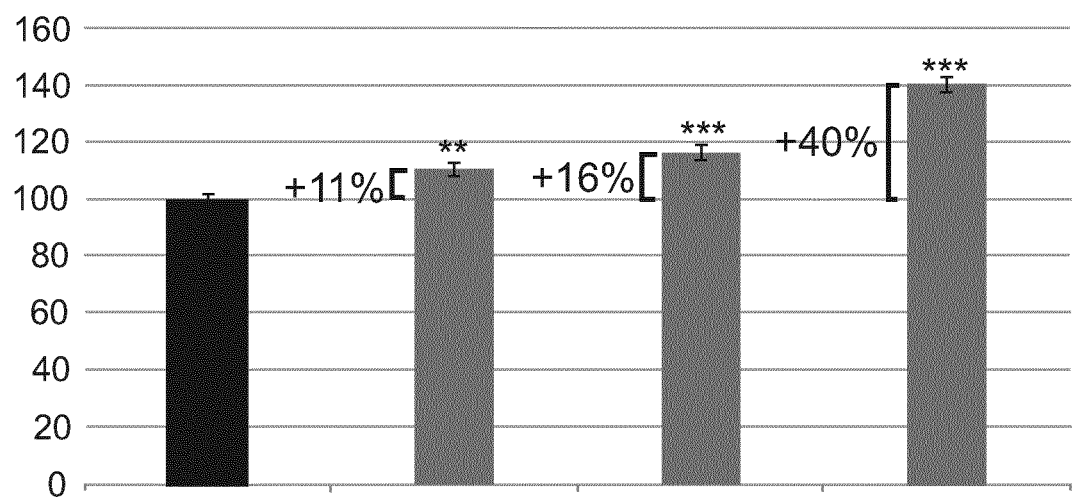
FIG. 6 shows the percentage increase in collagen VI synthesis by human dermal fibroblasts treated with growing concentrations of peptide Pal-SEQ ID NO: 1-$NH_2$ in comparison with the negative control (treated with dimethyl sulfoxide).

FIG. 6 shows the percentage increase in collagen VI synthesis by human dermal fibroblasts treated with growing concentrations of peptide Pal-SEQ ID NO: 1-NH$_2$ in comparison with the negative control (treated with dimethyl sulfoxide) (this is, stablishing the collagen VI synthesis of the negative control as 100% and then performing the comparison with the collagen VI synthesis of the rest of the samples tested). For FIG. 6 columns from left to right in the x-axis correspond to: negative control (cells treated with dimethyl sulfoxide) and cells treated with 0.001 mg/mL, 0.005 mg/mL, 0.01 mg/mL of peptide Pal-SEQ ID NO: 1-NH$_2$, respectively. The y axis shows the percentage collagen VI synthesis (with regard to the negative control).  refers to a $p<0.01$; and * refers to a $p<0.001$.

Figure 7:
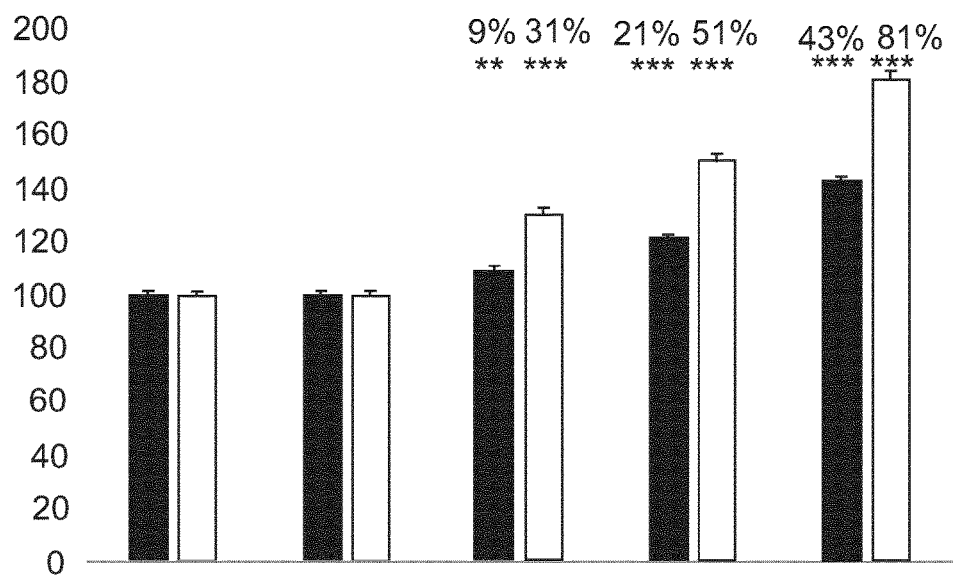
FIG. 7 shows the percentage increase of Mohawk synthesis by human dermal fibroblasts treated with growing concentrations of peptide Pal-SEQ ID NO: 1-$NH_2$ in comparison with the negative control (treated with dimethyl sulfoxide).

FIG. 7 shows the percentage increase of Mohawk synthesis by human dermal fibroblasts treated with growing concentrations of peptide Pal-SEQ ID NO: 1-NH$_2$ in comparison with the negative control (treated with dimethyl sulfoxide) (this is, stablishing the Mohawk synthesis of the negative control as 100% and then performing the comparison with the Mohawk synthesis of the rest of the samples tested). For FIG. 7 columns in black refer to 24 hours of treatment and columns in white refer to 48 hours of treatment. In addition, each group of two columns (one black and one white) from left to right in the x-axis in this figure correspond to: negative control (cells treated with dimethyl sulfoxide), untreated cells, and cells treated with 0.001 mg/mL, 0.005 mg/mL, 0.01 mg/mL of peptide Pal-SEQ ID NO: 1-NH$_2$, respectively. They axis shows the percentage Mohawk synthesis (with regard to the negative control).  refers to a $p<0.01$; and * refers to a $p<0.001$.

Figure 8:
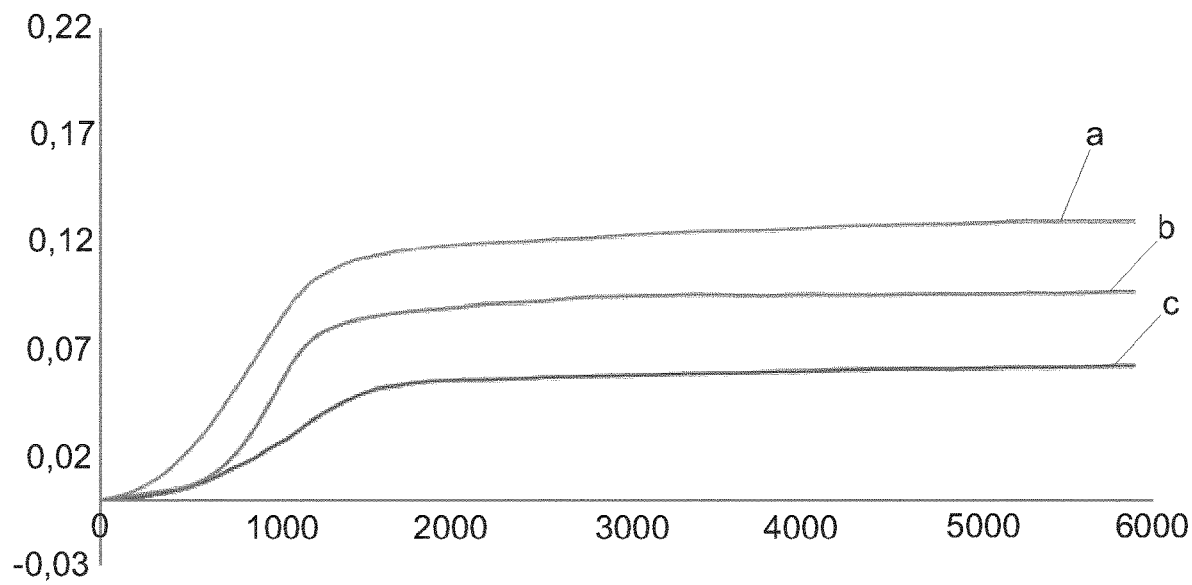
FIG. 8 shows the cross-linking of collagen.

FIG. 8 shows the cross-linking of collagen. Line noted with an "a" refers to cells treated with peptide Pal-SEQ ID NO: 1-NH$_2$ at a concentration of 0.04 mg/mL; line noted with a "b" refers to cells treated with peptide Pal-SEQ ID NO: 1-NH$_2$ at a concentration of 0.02 mg/mL; and line noted with "c" refers to cells treated with dimethyl sulfoxide (negative control). The x-axis shows the time in seconds and the y-axis shows the optical density in Absorbance Units at 450 nm.

Figure 9:
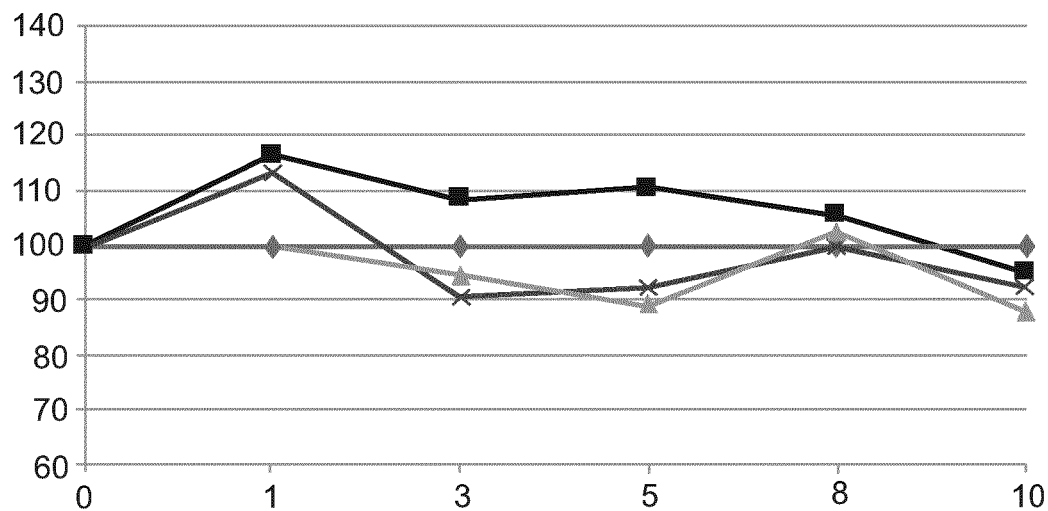
FIG. 9 shows the tissue viability by means of the percentage of released LDH (lactate dehydrogenase) in comparison with the negative control (untreated hOSECs).

FIG. 9 shows the tissue viability by means of the percentage of released LDH (lactate dehydrogenase) in comparison with the negative control (untreated hOSECs) (this is, stablishing the released LDH of the negative control as 100% and then performing the comparison with LDH released in the rest of the samples tested in example 11). The line with rhombus refers to untreated hOSECs (negative control); the line with squares refers to aged hOSECs; the line with triangles refers to aged hOSECs+product A (cream); and the line with crosses refers to aged hOSECs+ product B (cream with 0.005 mg/mL of peptide Pal-SEQ ID NO: 1-NH$_2$). The x-axis refers to the time in days; and the y-axis refers to the % of LDH released with regard to the negative control (untreated hOSECs).

Figure 10:
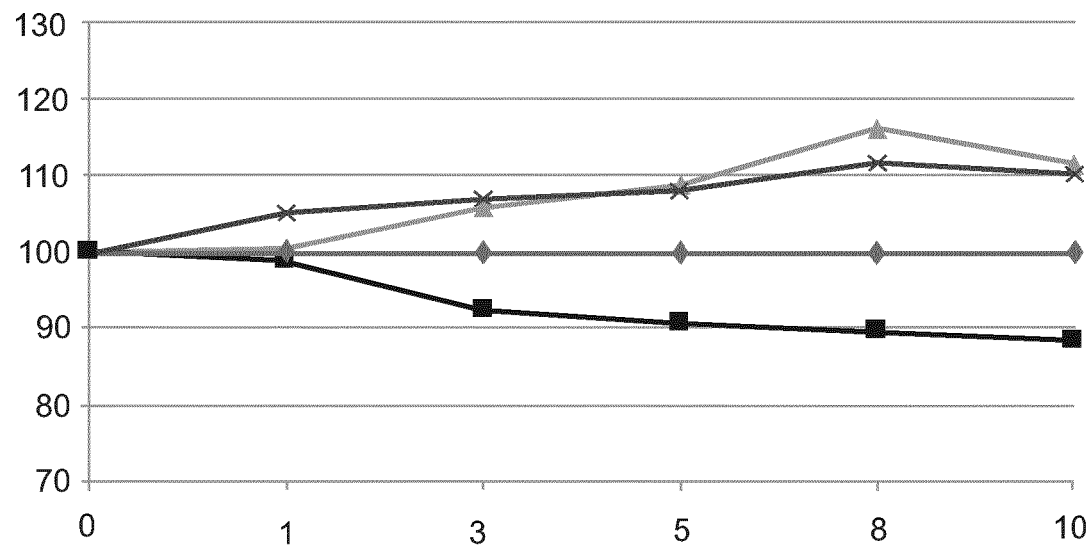
FIG. 10 shows the metabolism activity by means of the percentage of resorufin in comparison with the negative control (untreated hOSECs).

FIG. 10 shows the metabolism activity by means of the percentage of resorufin in comparison with the negative control (untreated hOSECs) (this is, stablishing the resorufin of the negative control as 100% and then performing the comparison with resorufin in the rest of the samples tested in example 11). The line with rhombus refers to untreated hOSECs (negative control); the line with squares refers to aged hOSECs; the line with triangles refers to aged hOSECs+product A (cream); and the line with crosses refers to aged hOSECs+product B (cream with 0.005 mg/mL of peptide Pal-SEQ ID NO: 1-NH$_2$), respectively. The x-axis refers to the time in days; and the y-axis refers to the % of resorufin with regard to the negative control (untreated hOSECs).

Figure 11:
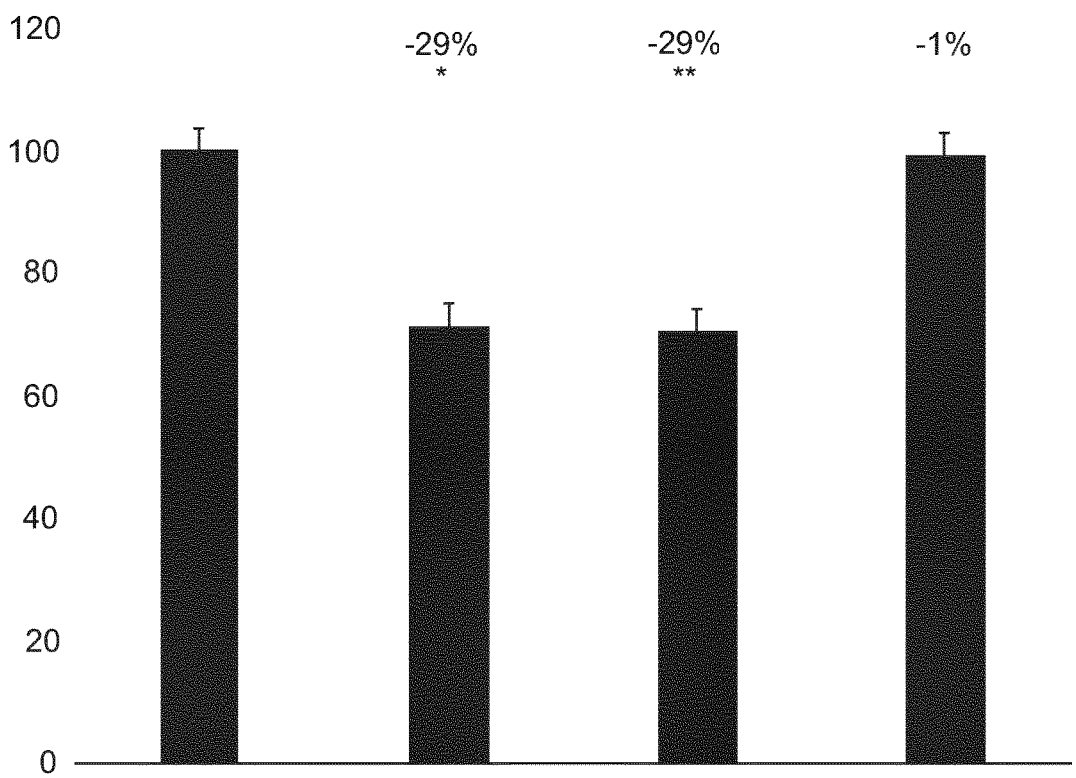
FIG. 11 shows the collagen quantification in the different experimental groups of example 11 in comparison with the negative control (untreated hOSEC).

FIG. 11 shows the collagen quantification in the different experimental groups of example 11 in comparison with the negative control (untreated hOSEC) (this is, stablishing the collagen quantity of the negative control as 100% and then performing the comparison with the collagen quantity of the rest of the samples tested). Columns from left to right in the x-axis correspond to: untreated hOSECs (negative control); aged hOSECs; aged hOSECs+product A (cream); and aged hOSECs+product B (cream with 0.005 mg/mL of peptide Pal-SEQ ID NO: 1-NH$_2$), respectively. The y-axis refers to the percentage of collagen quantity with regard to the negative control. * refers to a p<0.05; and ** refers to a p<0.01.

Figure 12:
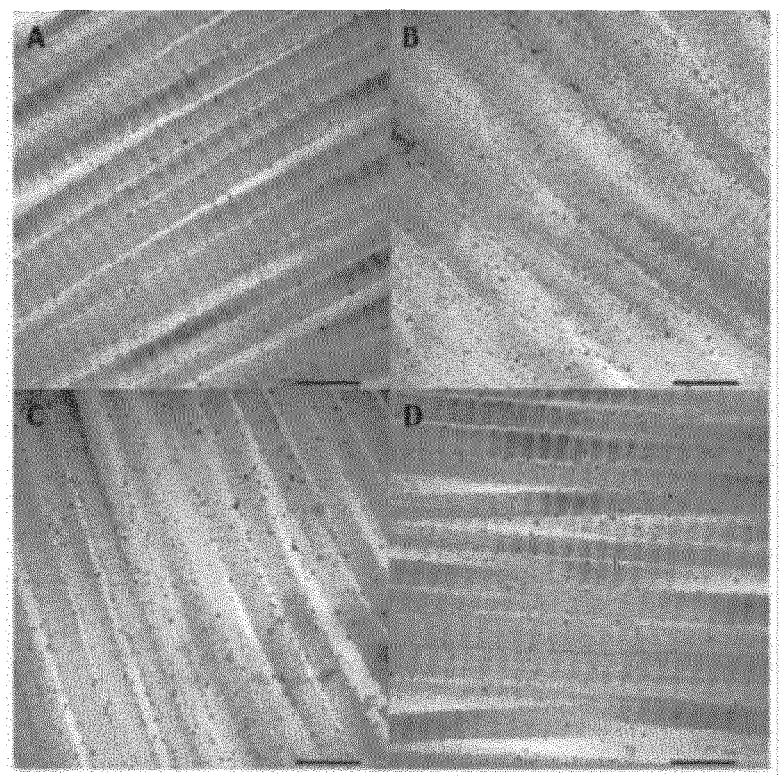
FIG. 12A shows transmission electron microscopy images of the different experimental groups of example 11, corresponding to untreated hOSEC.
FIG. 12B shows transmission electron microscopy images of the different experimental groups of example 11, corresponding to aged hOSE.
FIG. 12C shows transmission electron microscopy images of the different experimental groups of example 11, corresponding to aged hOSEC treated with the Product A (cream).
FIG. 12D shows transmission electron microscopy images of the different experimental groups of example 11, corresponding to aged hOSEC treated with product B (cream with 0.005 mg/mL of peptide Pal-SEQ ID NO: 1-$NH_2$).

FIG. 12 shows transmission electron microscopy images of the different experimental groups of example 11. More precisely, FIG. 12A corresponds to untreated hOSEC; FIG. 12B corresponds to aged hOSEC; FIG. 12C corresponds to aged hOSEC treated with the Product A (cream); and FIG. 12D corresponds to aged hOSEC treated with product B (cream with 0.005 mg/mL of peptide Pal-SEQ ID NO: 1-NH$_2$).

Figure 13:
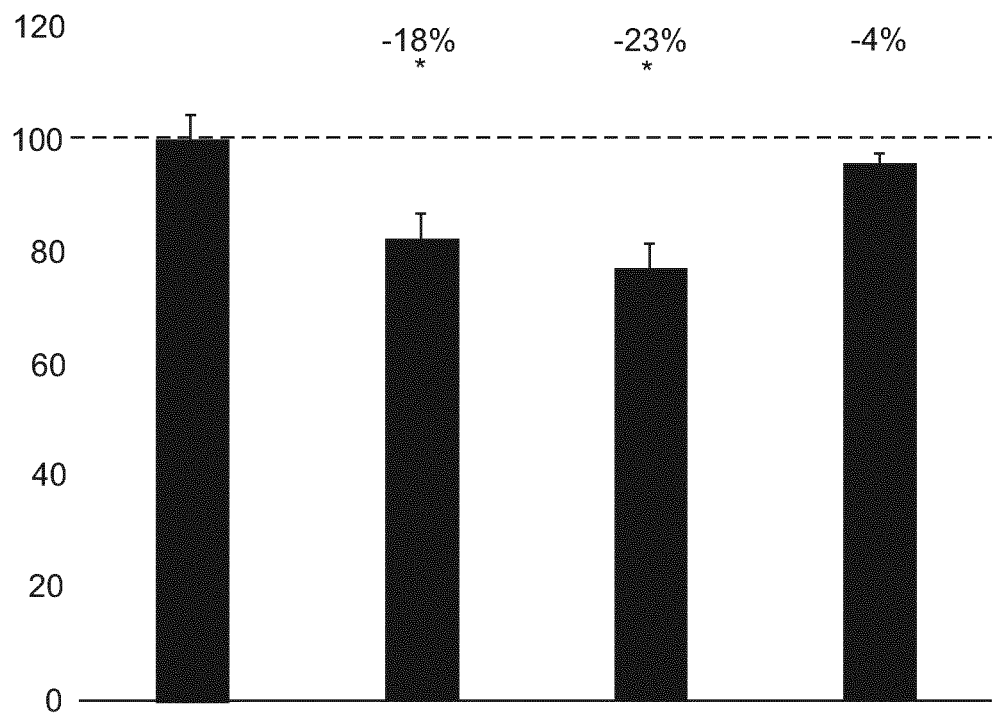
FIG. 13 shows the collagen density in the different experimental groups of example 11 in comparison with the negative control (untreated hOSEC).

FIG. 13 shows the collagen density in the different experimental groups of example 11 in comparison with the negative control (untreated hOSEC) (this is, stablishing the collagen density of the negative control as 100% and then performing the comparison with the collagen density of the rest of the samples tested). Columns from left to right in the x-axis correspond to: untreated hOSECs (negative control); aged hOSECs; aged hOSECs+product A (cream); and aged hOSECs+product B (cream with 0.005 mg/mL of peptide Pal-SEQ ID NO: 1-NH$_2$), respectively. The y-axis refers to the percentage of collagen density with regard to the negative control. * refers to a p<0.05.

Figure 14:
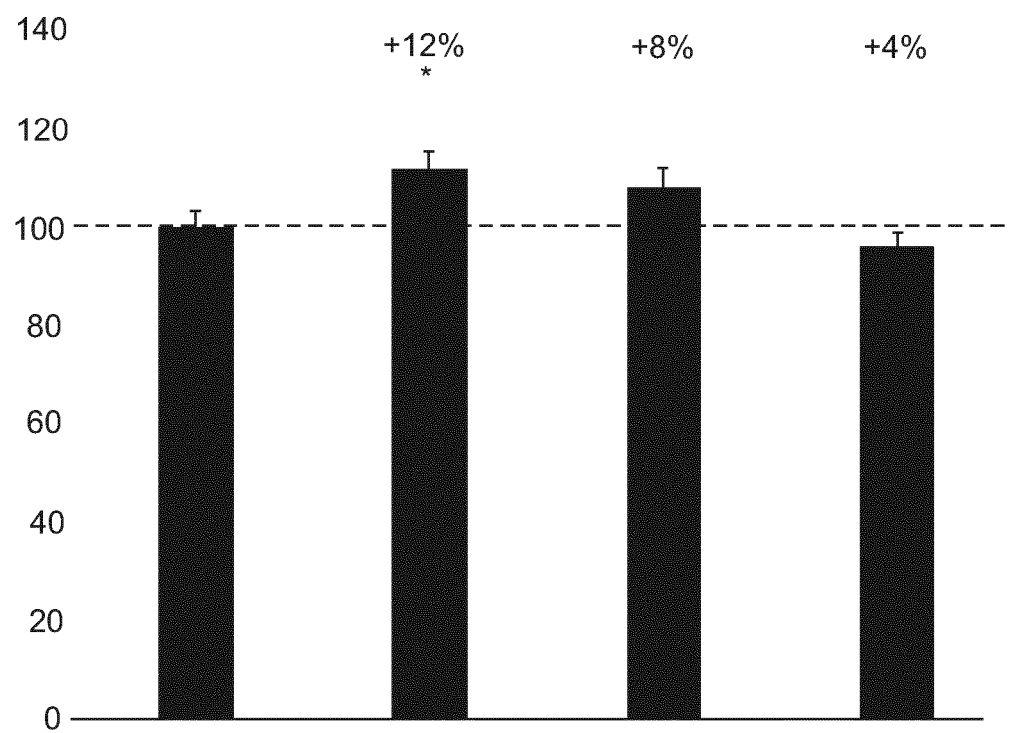
FIG. 14 shows the collagen fibre thickness in the different experimental groups of example 11 in comparison with the negative control (untreated hOSEC).

FIG. 14 shows the collagen fibre thickness in the different experimental groups of example 11 in comparison with the negative control (untreated hOSEC) (this is, stablishing the collagen fibre thickness of the negative control as 100% and then performing the comparison with the collagen fibre thickness of the rest of the samples tested). Columns from left to right in the x-axis correspond to: untreated hOSECs (negative control); aged hOSECs; aged hOSECs+product A (cream); and aged hOSECs+product B (cream with 0.005 mg/mL of peptide Pal-SEQ ID NO: 1-NH$_2$), respectively. The y-axis refers to the percentage collagen fibre thickness with regard to the negative control. * refers to a p<0.05.

Figure 15:
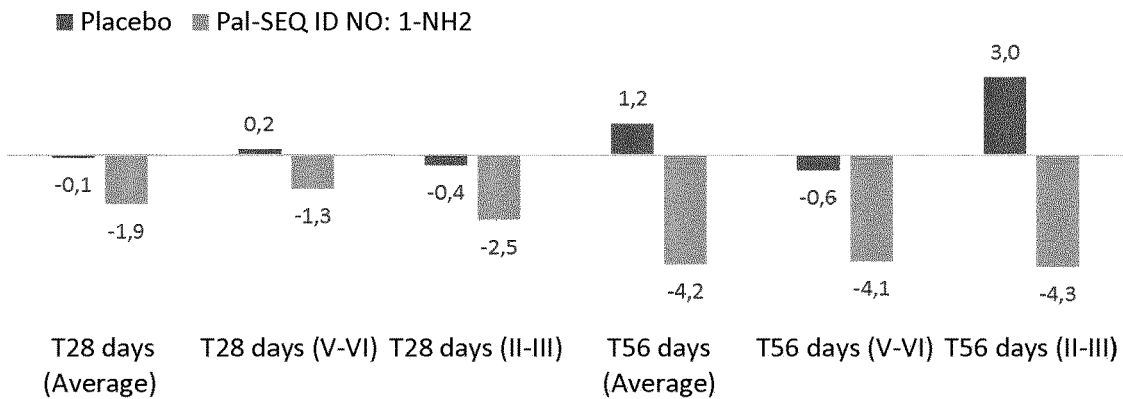
FIG. 15 shows the efficacy of Pal-SEQ ID NO: 1-$NH_2$ after its topical application on 44 female volunteers (50% light-pigmented (phototype II-III) and 50% dark-pigmented (phototype V-VI)).
Figure 15:
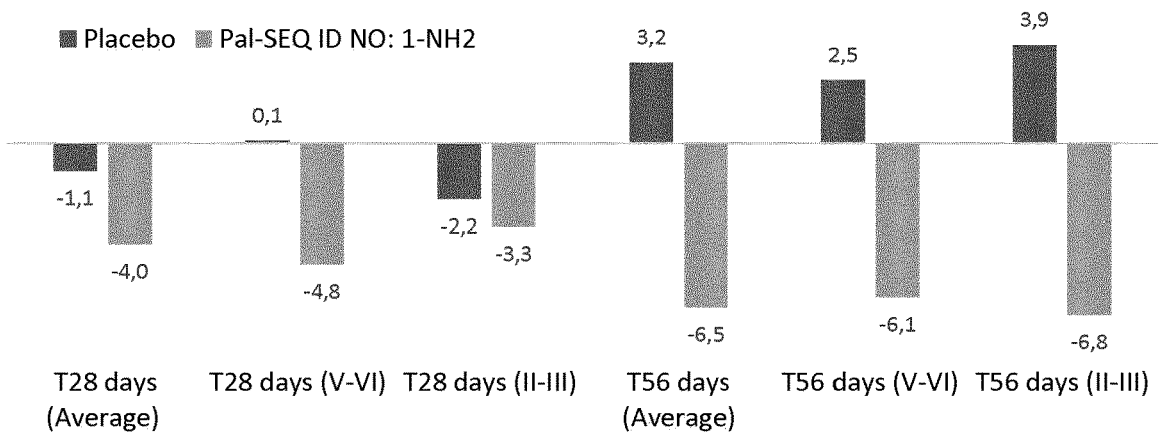
Figure 15:
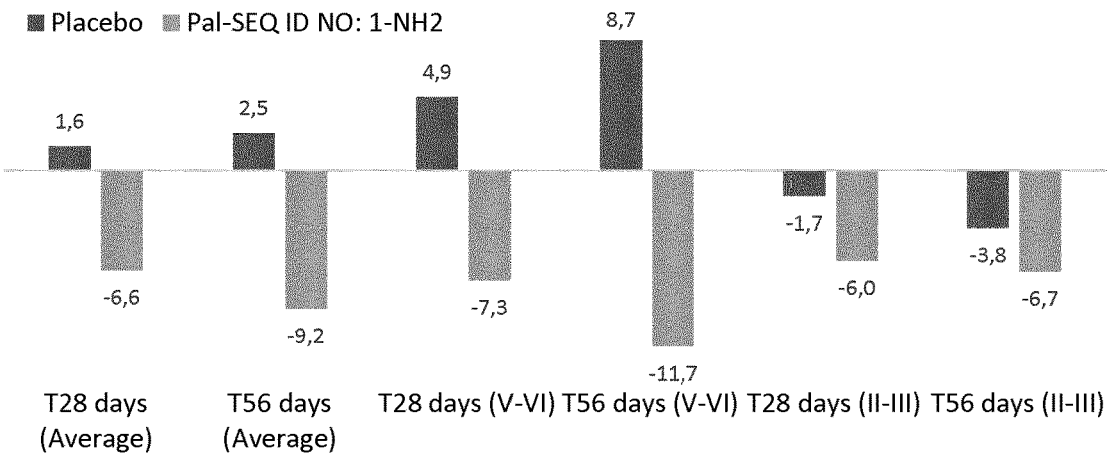

FIG. 15 shows the efficacy of Pal-SEQ ID NO: 1-NH$_2$ after its topical application on 44 female volunteers (50% light-pigmented (phototype II-III) and 50% dark-pigmented (phototype V-VI)). A cosmetic formulation comprising 2% (m/v) of Pal-SEQ ID NO: 1-NH$_2$ peptide from a stock at 0.05% (m/v) or a placebo were applied each on the whole face of a volunteer for 56 days. FIG. 15 (A) shows the roughness improvement of the cheek of the volunteers by AEVA (Eotech, France). AEVA evaluation is based on 3D images of the skin topography obtained by a stereo camera combined with a fringe projection system. In the x-axis, from left to right the groups of six columns each corresponds to: day 28 average of all volunteers, day 28 for phototype V-VI volunteers, day 28 for phototype II-III volunteers, day 56 average of all volunteers, day 58 for phototype V-VI volunteers and day 56 for phototype II-III volunteers all from the beginning of the treatment, respectively. Also in the x-axis, in each of the groups of columns, the columns, from left to right correspond to: volunteers treated with a cosmetic formulation (placebo) and with the same formulation but also comprising Pal-SEQ ID NO: 1-NH$_2$ peptide. The y axis shows the percentage of variation in the roughness parameter (Ra) versus initial time. FIG. 15 (B) shows the relief improvement of the cheek of the volunteers by AEVA. In the x-axis, from left to right the groups of six columns each corresponds to: day 28 average of all volunteers, day 28 for phototype V-VI volunteers, day 28 for phototype II-III volunteers, day 56 average of all volunteers, day 58 for phototype V-VI volunteers and day 56 for phototype II-III volunteers all from the beginning of the treatment, respectively. Also in the x-axis, in each of the groups of columns, the columns, from left to right correspond to: volunteers treated with a cosmetic formulation (placebo) and with the same formulation but also comprising Pal-SEQ ID NO: 1-NH$_2$ peptide. The y axis shows the percentage of variation in the relief parameter (Rz) versus initial time. FIG. 15 (C) shows the wrinkle depth variation (%) of the crow's feet area. In the x-axis, from left to right the groups of six columns each corresponds to: day 28 average of all volunteers, day 56 average of all volunteers, day 28 for phototype V-VI volunteers, day 56 for phototype V-VI volunteers, day 28 for phototype II-III volunteers and day 56 for phototype II-III volunteers, all from the beginning of the treatment, respectively. Also in the x-axis, in each of the groups of columns, the columns, from left to right correspond to: volunteers treated with a cosmetic formulation (placebo) and with the same formulation but also comprising Pal-SEQ ID NO: 1-NH$_2$ peptide. They axis shows the percentage of variation in the wrinkle depth in crow's feet area versus initial time.

EXAMPLES

Abbreviations:

The abbreviations used for amino acids follow the 1983 IUPAC-IUB Joint Commission on Biochemical Nomenclature recommendations outlined in Eur. J. Biochem. (1984) 138:937.

Ac, acetyl; Ala, alanine; Arg, arginine; C-terminal, carboxy-terminal; DCM, dichloromethane; DIEA, N,N'-diisopropylethylamine; DIPCDI, N,N'-diisopropylcarbodiimide; DMF, N,N-dimethylformamide; EDGS, EpiLife Defined Growth Supplement; equiv, equivalent; ESI-MS, electrospray ionization mass spectrometry; Fmoc, 9-fluorenylmethyloxycarbonyl; His, histidine; HOBt, 1-hydroxybenzotriazole; hOSEC, human organotypical skin explant culture; HPLC, high performance liquid chromatography; HRP, Horseradish peroxidase; Ile, Isoleucine; LSGS, Low Serum Growth Supplement; MBHA, p-methylbenzhydrylamine; Leu, leucine; Lys, lysine; Me, methyl; MeCN, acetonitrile; MeOH, methanol; Met, Methionine; N-terminal, amino-terminal; Pal, palmitoyl; Pbf, 2,2,4,6,7-pentamethyldihydrobenzofuran-5-sulfonyl; Phe, Phenylalanine; rpm, revolutions per minute; RT, room temperature; tBu, tent-butyl; TFA, trifluoroacetic acid; TIS, triisopropylsilane; TMB, 3,3',5,5'-Tetramethylbenzidine; Trt, triphenylmethyl or trityl; Trp, Tryptophan; Tyr, Tyrosine; Val, Valine.

Regarding the chemical synthesis procedures included in the examples, it is noted that all synthetic processes were carried out in polypropylene syringes fitted with porous polyethylene discs or Pyrex® reactors fitted with porous plates. All the reagents and solvents were synthesis quality and were used without any additional treatment. The solvents and soluble reagents were removed by suction. The Fmoc group was removed with piperidine-DMF (2:8, v/v) (at least 1×1 min, 2×10 min, 5 mL/g resin) (Lloyd Williams P. et al, (1997), Chemical Approaches to the Synthesis of Peptides and Proteins. CRC, Boca Raton (Fla., USA)). Washes between stages of deprotection, coupling, and, again, deprotection, were carried out with DMF (3×1 min) and DCM (3×1 min) each time using 10 ml solvent/g resin. Coupling reactions were performed with 3 ml solvent/g resin. The control of the couplings was performed by carrying out the ninhydrin test (Kaiser E. et al., Anal. Biochem., 1970, 34: 595598). All synthetic reactions and washes were carried out at RT.

Example 1. Synthesis and Preparation of the Peptides

Obtaining Fmoc-$AA_1$-$AA_2$-$AA_3$-$AA_4$-Rink-MBHA-resin, wherein $AA_1$ is L-His; $AA_2$ is L-Tyr; $AA_3$ is L-Ara; and $AA_4$ is L-Ala Weights were normalized. 4.8 g (2.5 mmol) of the Fmoc-Rink-MBHA resin with a functionalization of 0.52 mmol/g were treated with piperidine-DMF according to the described general protocol known in the state of the art in order to remove the Fmoc group. 2.33 g of Fmoc-L-Ala-OH (7.5 mmol; 3 equiv) were incorporated onto the deprotected resin in the presence of DIPCDI (1.17 mL; 7.5 mmol; 3 equiv) and HOBt (1.01 g; 7.5 mmol; 3 equiv) using DMF as a solvent for one hour.

The resin was then washed as described in the general methods known in the state of the art and the deprotection treatment of the Fmoc group was repeated to couple the next amino acid. Following the previously described protocols 4.87 g of Fmoc-Arg(Pbf)-OH (7.5 mmol; 3 equiv); subsequently 3.45 g of Fmoc-L-Tyr(tBu)—OH (7.5 mmol; 3 equiv); and subsequently 4.65 g of Fmoc-L-His(Trt)-OH (7.5 mmol; 3 equiv) were coupled, sequentially, each coupling in the presence of 1.01 g of HOBt (7.5 mmol; 3 equiv) and 1.17 mL of DIPCDI (7.5 mmol; 3 equiv). As already noted above, between each amino acid addition step, a deprotection treatment of the Fmoc group was performed.

After the synthesis, the peptide resins were washed with DCM (5 times for 3 minutes each one) and dried under vacuum.

Using the synthesis procedure mentioned above, the following sequence was synthesized:

His-Tyr-Arg-Ala (SEQ ID NO: 1).

Example 2. Removal of Fmoc N-Terminal Protective Group of the Peptides Synthesized in Accordance with Example 1

The N-terminal Fmoc group of the peptidyl resins was deprotected with 20% (volume/volume, hereinafter v/v) piperidine in DMF (1×1 min+2×10 min) (Lloyd Williams P. et al. (1997) Chemical Approaches to the Synthesis of Peptides and Proteins. CRC, Boca Raton (Fla., USA)). The peptidyl resins were washed with DMF (5×1 min), DCM (4×1 min), and dried under vacuum.

Example 3. Process for Introducing the $R_1$ Palmitoyl Group onto the Peptidyl Resins Obtained in Accordance with Example 2

1 mmol (1 equiv) of the peptidyl resins obtained in accordance with Example 2 was treated with 10 equivalents of hexadecenoic acid (palmitic acid) in the presence of 10 equivalents of DIEA and 10 equivalents of HOBt using 5 mL of DMF as a solvent. They were left to react for 30 minutes, after which the peptidyl resins were washed with DMF (5×1 min), DCM (4×1 min), and were dried under vacuum.

Example 4. Cleavage Process from the Polymeric Support of the Peptidyl Resins Obtained in Accordance with Example 2 and 3

Weights were normalized. 200 mg of the dried peptidyl resin obtained in any of Examples 2 or 3 were treated with 5 mL of TFA/TIS/$H_2O$ (90:5:5) for 2 hours at room temperature under stirring. The filtrates were collected and precipitated using 50 mL (8 to 10-fold) of cold diethyl ether. The ethereal solutions were evaporated to dryness at reduced pressure and room temperature, the precipitates were redissolved in 50% (v/v) MeCN in $H_2O$ and lyophilized.

Example 5. Characterization of the Peptides Synthesized and Prepared in Accordance with Example 4

HPLC analysis of the peptides obtained in accordance with example 4 was carried out with a Shimadzu equipment (Kyoto, Japan) using a reverse-phase column (150×4.6 mm, XBridge Peptide BEH C18, 3.5 μm, Waters, USA) in gradients of MeCN (+0.036% (v/v) TFA) in $H_2O$ (+0.045% (v/v) TFA) at a flow rate of 1.25 mL/min and detection was carried out at 220 nm. All peptides showed a purity exceeding 80%. The identity of the peptides obtained was confirmed by ESI-MS in a Water ZQ 4000 detector using MeOH as the mobile phase and a flow rate of 0.2 mL/min. Results obtained demonstrated that peptide Pal-His-Tyr-Arg-Ala-$NH_2$ (Pal-SEQ ID NO: 1-$NH_2$) was correctly and effectively synthesized.

Example 6. Analysis of Cytotoxicity of the Peptide Pal-SEQ ID NO: 1-NH$_2$ in HEKa and HDFa Cells The cytotoxicity of peptide Pal-SEQ ID NO: 1-NH$_2$ was analysed by means of viability assay in HEKa (Human Epidermal Keratinocytes, adult) and HDFa (Human Dermal Fibroblasts, adult) cells.

Peptide Pal-SEQ ID NO: 1-NH$_2$ was prepared in accordance with examples 1 to 5.

Cytotoxicity was assessed by means of the MTT assay. Briefly HEKa and HDFa cells were seeded in 96-well plates at a concentration of 1×10$^5$ cells/mL and incubated in Epilife Medium supplemented with 1% (v/v) EDGS and 1% (v/v) of Penicillin/Streptomycin (for HEKa cells) and Medium 106 supplemented with 2% (v/v) of Low Serum Growth Supplement (LSGS) (for HDFa cells) for 24 h at 37° C., 5% CO$_2$ and saturated humidity. Cells were then treated with different concentrations of peptide Pal-SEQ ID NO: 1-NH$_2$ (0.001 mg/mL, 0.005 mg/mL, 0.01 mg/mL, 0.05 mg/mL, and 0.1 mg/mL for HEKa cells; and 0.001 mg/mL, 0.005 mg/mL and 0.01 mg/mL for HDFa cells) in triplicates, for MTT evaluation. After 24 h of treatment with the peptide at the corresponding concentration, 10 μL of the yellow tetrazolium (MTT) were added to each well and the cells were incubated at 37'C for additional 4 h. After incubating with MTT, the medium of each well was aspirated and 150 μL of dimethyl sulfoxide (hereinafter DMSO) (100%) were added in order to solubilise the formazan crystals formed. The plates were placed on a shaker for 5 minutes for complete solubilisation of the crystals and then the absorbance at 450 nm of each well was determined using the microplate reader Multiskan FC, which is directly proportional to the number of living cells in culture. Absorbance values were normalized using the data obtained for non-treated cells (basal state).

Results appear summarized in FIGS. 1 and 2.

As can be directly derived from said figures, the peptides of the present invention (as exemplified by means of Pal-SEQ ID NO: 1-NH$_2$) did not alter viability of HEKa and HDFa cells at the tested concentrations and, hence, are not cytotoxic.

Example 7. Analysis Gene Expression Modulation in Primary Human Dermal Fibroblasts Peptide Pal-SEQ ID NO: 1-NH$_2$ was analysed for its capacity to modulate expression of genes related with the production of collagen and the extracellular matrix (see table 1 for the analysed genes).

Peptide Pal-SEQ ID NO: 1-NH$_2$ was prepared in accordance with examples 1 to 5.

A stock solution of the peptide was prepared in DMSO at 12.5 mg/mL. Working solution was freshly prepared at the specified concentration from stock solution in the corresponding supplemented medium.

Untreated cells were used as negative control samples.

RNA (ribonucleic acid) extraction and RT-qPCR (reverse transcription quantitative polymerase chain reaction) were performed. Briefly, HDFa cells were seeded in duplicate (n=2) in 6-well plates at a density of 4×10$^5$ cells/well and maintained at standard culture conditions (106 Medium supplemented with 1% (v/v) LSGS; 37° C., 95% room humidity, 5% CO$_2$) for 24 hours. Then, cells were treated with peptide Pal-SEQ ID NO: 1-NH$_2$ at the concentration of 0.005 mg/mL for additional 6 hours (or 24 hours, for COL13A1). Untreated cells were used as basal control.

Cells were finally lysed, and replicates were pooled together for RNA extraction using Qiagen RNeasy Mini kit following manufacturer's instructions. Purified RNAs were used to generate the corresponding cDNAs (complementary deoxyribonucleic acids) by reverse transcription using a commercial kit High capacity cDNA reverse transcription kit (Applied Biosystems) which served as templates for amplification. RT-qPCR was performed with the panel of appropriate TaqMan assay probes for genes shown in table 1 (plus GAPDH-Glyceraldehyde 3-phosphate dehydrogenase—that was used as housekeeping gene) and 2× gene expression Master Mix using StepOne plus Real-Time PCR instrument. Amplification included 40 cycles of 15 seconds at 95° C. (denaturation) and 1 minute at 60° C. (Annealing and extension) (Arya, M., Shergill, I. S., Williamson, M., Gommersall, L., Arya, N., Patel, H. R. (2005) *Basic principles of real-time quantitative PCR*. Expert Rev. Mol. Diagn.; 5(2):209-19; and Jozefczuk, J. and Adjaye, J. (2011) *Quantitative real-time PCR-based analysis of gene expression*. Methods Enzymol. 500; 99-109).

TABLE 1

Genes analysed in example 7.

| Abbreviation | Gene |
| --- | --- |
| TGFB1 | Transforming growth factor beta-1 |
| FN1 | Fibronectin 1 |
| LOXL3 | Lysyl oxidase like 3 |
| LOXL2 | Lysyl oxidase like 2 |
| HSP47 | Serpin H1 |
| COL3A1 | Collagen Type III Alpha 1 Chain |
| COL4A5 | Collagen Type IV Alpha 5 Chain |
| COL5A1 | Collagen Type V Alpha 1 Chain |
| COL6A1 | Collagen Type VI Alpha 1 Chain |
| COL7A1 | Collagen Type VII Alpha 1 Chain |
| COL12A1 | Collagen Type XII Alpha 1 Chain |
| COL14A1 | Collagen Type XIV Alpha 1 Chain |
| COL13A1 | Collagen Type XIII Alpha 1 Chain |
| MKX | Mohawk homeobox |
| ZEB2 | Zinc Finger E-Box Binding Homeobox 2 |
| MMP1 | Matrix metalloproteinase-1 |
| MMP3 | Matrix metalloproteinase-3 |

The obtained data was analysed using the ΔΔCt method, which provides the target gene expression values as fold changes in the treated sample compared with an untreated basal sample. Both samples were normalized with the relative expression of a housekeeping gene GAPDH (Glyceraldehyde 3-phosphate dehydrogenase).

The steps for analysis included:
1. Calculate the average Ct for each condition
2. Calculate the ΔCT test sample and the ΔCT untreated sample
3. Calculate the ΔΔCT: ΔΔCT=ΔCT test sample−ΔCT untreated sample
4. Obtain ratio by $2^{-\Delta\Delta CT}$ The results of this assay appear summarized in FIGS. 3 to 5.

As can be readily derived from said figures, peptide Pal-SEQ ID NO: 1-NH$_2$:

After 6 hours of treatment: downregulates genes MMP1 and MMP3, which, as it is widely known, degrade extracellular matrix proteins.

After 6 hours of treatment upregulates several key genes in collagen architecture and extracellular architecture: COL3A1, COL4A5, COL5A1, COL6A1, COL7A1, COL12A1, COL14A1, COL13A1 (after 24 hours of treatment), MKX y ZEB2.

Upregulates several collagen crosslinking-related genes after 6 hours of treatment: TGFB1, FN1, LOXL3, LOXL2 and HSP47.

Therefore, the peptides of the present invention (as exemplified by means of Pal-SEQ ID NO: 1-$NH_2$) avoid or prevent extracellular matrix degradation while contributing to an increases synthesis and cross-linking of collagen, showing, hence, an antiaging activity and rejuvenating activity.

Example 8. Analysis of Collagen VI Synthesis in Human Dermal Fibroblasts

Peptide Pal-SEQ ID NO: 1-$NH_2$ was analysed for its capacity to induce synthesis collagen Peptide Pal-SEQ ID NO: 1-$NH_2$ was prepared in accordance with examples 1 to 5.

In this assay, it was evaluated in vitro the capability of the tested peptide to increase collagen VI synthesis in human dermal fibroblasts. This evaluation was carried out by determination of collagen VI amount after cell treatment with Pal-SEQ ID NO: 1-$NH_2$.

Experimental protocol provided for the following experimental groups:
- negative control: cell culture treated only with solubilisation vehicle (DMSO);
- cell culture treated with peptide Pal-SEQ ID NO: 1-$NH_2$ at three concentrations (0.01 mg/mL, 0.005 mg/mL and 0.001 mg/mL).

A stock solution of the peptide in DMSO was prepared and then three serial dilutions at 0.01 mg/mL, 0.005 mg/mL and 0.001 mg/mL in cell culture medium were prepared.

The biological model used in this case consisted of normal human dermal fibroblasts. Cells were seeded in 96-well plate at $1 \times 10^4$ cells/well and maintained for 24 h at standard culture conditions (37° C., 95% room humidity, 5% $CO_2$).

After 24 h incubation, medium was removed and new medium containing the treatment (DMSO or Pal-SEQ ID NO: 1-$NH_2$) was added to the wells. Sample treatment lasted 48 hours and at the end of treatment cell culture media were collected. Cells treated with DMSO were used as negative control.

For the test execution, cell culture of human dermal fibroblasts were treated with Pal-SEQ ID NO: 1-$NH_2$ at the three concentrations noted above.

After a 48-hour treatment the amount of collagen VI produced and released by the cells (ex-novo collagen VI synthesis) was measured in cell culture medium by means of ELISA assay. The results were compared to those of the negative control (cells treated with DMSO). The treatments were performed in triplicate and in three different experimental sessions.

The determination of collagen VI synthesis was carried out by means of ELISA method. Commercial kits were used for this purpose. The test kit used Sandwich-ELISA method to detect the content of human collagen VI. The micro ELISA plate provided in the kit was pre-coated with an antibody specific to collagen VI. Standards or samples were added to the appropriate micro ELISA plate wells and combined with the specific antibody. Then, a biotinylated detection antibody specific for collagen VI and Avidin-Horseradish Peroxidase (HRP) conjugate were added to each micro plate well successively and incubated. Free components were washed away. The substrate solution (TMB) was added to each well.

Only those wells that contained collagen VI developed a blue color. The enzyme-substrate reaction was terminated by the addition of a sulphuric acid solution and the color turned yellow. The optical density (OD) was measured by microplate reader at a wavelength of 450 nm. The OD value was proportional to the concentration of collagen VI.

The quantitative determination used a calibration curve made-up of known and growing concentrations of standard collagen VI. The % variation in collagen VI content between negative control (DMSO) and sample was calculated, which is a direct index of the efficacy of Pal-SEQ ID NO: 1-$NH_2$ to increase collagen VI synthesis.

The results obtained in this experiment appear summarized in table 2 and in FIG. 6.

TABLE 2

Mean results for the collagen VI content in example 8 for the different groups as well as percentage variation of said content with regard to the negative control group.

| Group | Collagen VI content (ng/mL) | % variation with regard to the negative control |
|---|---|---|
| Negative control | 11.06 ± 0.75 | — |
| cell culture treated with peptide Pal-SEQ ID NO: 1-$NH_2$ at 0.01 mg/mL | 15.52 ± 0.80 | 40% |
| cell culture treated with peptide Pal-SEQ ID NO: 1-$NH_2$ at 0.005 mg/mL | 12.87 ± 0.97 | 16% |
| cell culture treated with peptide Pal-SEQ ID NO: 1-$NH_2$ at 0.001 mg/mL | 12.22 ± 0.78 | 11% |

As can be directly derivable from table 2 and FIG. 6, in all cases (this is, for all concentrations tested) a statistically significant increase in the synthesis of collagen VI was observed, which, moreover, could be described as dose dependent: increase of 11% at 0.001 mg/mL, of 16% at 0.005 mg/mL and of 40% at 0.01 mg/mL. As noted in FIG. 6, the differences seen in collagen VI content in the treated groups with regard to the negative control are statistically significant.

The above results demonstrate that the peptides of the present invention (as exemplified by Pal-SEQ ID NO: 1-$NH_2$) increase the synthesis of the protein collagen VI and, hence, contribute to improve extracellular matrix assembly. Therefore, said peptides can prevent or treat aging of the skin and/or the skin signs of said aging as, for example, wrinkles, roughness and/or sagginess.

In addition, the results of this example also demonstrate that the peptides of the present invention (as exemplified by Pal-SEQ ID NO: 1-$NH_2$) are able to provide for skin rejuvenation and/or to reduce, prevent and/or eliminate skin imperfections, more precisely, the peptides of the present invention (as exemplified by Pal-SEQ ID NO: 1-$NH_2$) are able to provide for facial repositioning and/or facial skin tightening.

Example 9. Analysis of Mohawk Synthesis in Human Dermal Fibroblasts

Peptide Pal-SEQ ID NO: 1-$NH_2$ was analysed for its capacity to induce synthesis of Mohawk in human dermal fibroblasts.

Peptide Pal-SEQ ID NO: 1-$NH_2$ was prepared in accordance with examples 1 to 5.

This assay concerns the in vitro evaluation of the capability of peptide Pal-SEQ ID NO: 1-NH$_2$ to increase Homeodomain protein Mohawk synthesis in human dermal fibroblasts. This evaluation was carried out by determination of Mohawk amount after cell treatment with said peptide.

The experimental protocol provided for the following experimental groups:
- untreated cell culture;
- cell culture treated only with solubilisation vehicle (DMSO) (negative control);
- cell culture treated with Pal-SEQ ID NO: 1-NH$_2$ at three concentrations (0.01 mg/mL, 0.005 mg/mL and 0.001 mg/mL).

A stock solution of the peptide in DMSO was prepared and then three serial dilutions at 0.01 mg/mL, 0.005 mg/mL and 0.001 mg/mL in cell culture medium were prepared.

The biological model used, as noted above, consists of normal human dermal fibroblasts.

Cells were seeded in 96-well plate at 1×10$^4$ cells/well and maintained for 24 h at standard culture conditions (37° C., 95% room humidity, 5% CO$_2$). After 24 h incubation, medium was removed and new medium containing tested product was added to the wells.

Sample treatment lasted 24 h and 48 h and then cells were lysed in order to determine the concentration of intracellular Mohawk by means of ELISA assay. The results were compared to negative control (cells treated with DMSO).

The treatments were performed in triplicate in three different experimental sessions.

The determination of Mohawk synthesis, as noted above, was carried out by means of ELISA method. Commercial kits were used for this purpose. The test kit applied a two-site sandwich ELISA method to detect the content of human Homeodomain protein Mohawk. An antibody specific for Mohawk had been pre-coated onto a microplate. Standards and samples were pipetted into the wells and any Mohawk present was bound by the immobilized antibody. After removing any unbound substances, HRP-Conjugated Human Mohawk detection antibody was added to the wells. Following a wash to remove any unbound HRP reagent, a chromogen solution was added to the wells (substrate was TMB) and color developed in proportion to the amount of Mohawk bound in the initial step. The color development was stopped and the concentration was determined colorimetrically at 450 nm.

The quantitative determination used a calibration curve made-up of known and growing concentrations of standard Mohawk. The % variation in Mohawk content between negative control (DMSO) and the group treated with Pal-SEQ ID NO: 1-NH$_2$ was calculated and was a direct index of the efficacy of peptide Pal-SEQ ID NO: 1-NH$_2$ to increase Mohawk synthesis.

The results obtained appear summarized in table 3 and FIG. 7.

TABLE 3

Mean results for the Mohawk content in example 9 for the different groups as well as percentage variation of said content with regard to the negative control group.

| Group | Time (h) | Mohawk content (pg/mL) | % variation with regard to the negative control |
|---|---|---|---|
| Untreated cells | 24 | 137.40 ± 6.87 | — |
| Negative control | 24 | 136.14 ± 5.44 | — |
| cell culture treated with peptide Pal-SEQ ID NO: 1- NH$_2$ at 0.01 mg/mL | 24 | 194.37 ± 7.30 | 43% |
| cell culture treated with peptide Pal-SEQ ID NO: 1- NH$_2$ at 0.005 mg/mL | 24 | 165.31 ± 7.24 | 21% |
| cell culture treated with peptide Pal-SEQ ID NO: 1- NH$_2$ at 0.001 mg/mL | 24 | 148.19 ± 8.44 | 9% |
| Untreated cells | 48 | 154.98 ± 9.91 | — |
| Negative control | 48 | 157.20 ± 7.57 | — |
| cell culture treated with peptide Pal-SEQ ID NO: 1- NH$_2$ at 0.01 mg/mL | 48 | 284.72 ± 13.51 | 81% |
| cell culture treated with peptide Pal-SEQ ID NO: 1- NH$_2$ at 0.005 mg/mL | 48 | 237.03 ± 10.44 | 51% |
| cell culture treated with peptide Pal-SEQ ID NO: 1- NH$_2$ at 0.001 mg/mL | 48 | 205.30 ± 11.53 | 31% |

As can be directly derivable from table 3 and FIG. 7, in all cases (this is, for all concentrations and durations tested) a statistically significant increase in the synthesis of homeodomain protein Mohawk was observed, which, moreover, could be described as dose and dependent: at 24 h increase of 9% at 0.001 mg/mL, of 21% at 0.005 mg/mL and of 43% at 0.01 mg/mL; and at 48 h increase of 31% at 0.001 mg/mL, of 51% at 0.005 mg/mL and of 81% at 0.01 mg/mL. As noted in FIG. 7, the differences seen in Mohawk content in the treated groups with regard to the negative control in each of the time frames tested are statistically significant.

The above results demonstrate that the peptides of the present invention (as exemplified by Pal-SEQ ID NO: 1-NH$_2$) increase the synthesis of Mohawk and, hence, its potential for the prevention or treatment of aging of the skin and/or the skin signs related with aging as, for example, wrinkles, roughness and/or sagginess.

In addition, the results of this example also demonstrate that the peptides of the present invention (as exemplified by Pal-SEQ ID NO: 1-NH$_2$) are able to provide for skin rejuvenation and/or to reduce, prevent and/or eliminate skin imperfections, more precisely, the peptides of the present invention (as exemplified by Pal-SEQ ID NO: 1-NH$_2$) are able to provide for facial repositioning and/or facial skin tightening.

Example 10. Analysis of Collagen Cross-Linking

Peptide Pal-SEQ ID NO: 1-NH$_2$ was analysed for its capacity to induce or improve collagen cross-linking.

Peptide Pal-SEQ ID NO: 1-NH$_2$ was prepared in accordance with examples 1 to 5.

This assay concerns the in tuba evaluation of the capability of peptide Pal-SEQ ID NO: 1-NH$_2$ to increase and accelerate collagen fibril formation/collagen cross-linking. This evaluation was carried out by determination of collagen fibril formation after collagen treatment with said peptide in solution (0.02 M acetic acid, 0.125 M NaCl and 1/10 phosphate buffered saline (pH=7.4)) at RT.

The experimental protocol provided for the following experimental groups:
collagen solution treated with Pal-SEQ ID NO: 1-$NH_2$ at two concentrations (0.02 or 0.04 mg/mL).
collagen solution only treated with the same solution as the treatment groups mentioned above but without the peptide, and hence, with the same volume of DMSO as the samples containing the peptide (negative control);

A stock solution of the peptide in DMSO was prepared and then two serial dilutions were prepared so that the final concentration of the peptide in the collagen solution was 0.02 mg/mL or 0.04 mg/mL.

The collagen cross-linking and fibril formation was followed immediately after addition of collagen to the control (same solution as the treatment groups but without the peptide, and hence, with the same volume of DMSO as the samples containing the peptide) and the solution containing Pal-SEQ ID NO: 1-$NH_2$ in the treated groups.

The results were compared to negative control (solution containing DMSO and no Pal-SEQ ID NO: 1-$NH_2$).

The experiments were performed in four different experimental sessions.

The determination of collagen cross-linking, was carried out by measurement of the absorbance at 450 nm.

Samples were pipetted into the wells and the absorbance at 450 nm of each well was determined every 2 min for a time period of 100 min using the microplate reader Multiskan FC.

The % variation in collagen fibril formation between negative control (group only treated with DMSO) and the groups treated with Pal-SEQ ID NO: 1-$NH_2$ was calculated and was a direct index of the efficacy of peptide Pal-SEQ ID NO: 1-$NH_2$ to increase collagen fibril formation, which, moreover, could be described as dose dependent: increase of 59% at 0.02 mg/mL and of 111% at 0.04 mg/mL.

The results obtained appear summarized in FIG. 8.

As can be derived from FIG. 8, peptide Pal-SEQ ID NO: 1-N $H_2$ increases and accelerates the cross-linking of Collagen at the two concentrations tested: 0.02 (b) and 0.04 (a) mg/mL.

The above gives support to the anti-ageing activity of the peptides of the present invention (as exemplified by means of Pal-SEQ ID NO: 1-$NH_2$) and, hence, their utility in preventing or treating skin signs related with aging as, for example, wrinkles, roughness and/or sagginess.

In addition, the results of this example also demonstrate that the peptides of the present invention (as exemplified by Pal-SEQ ID NO: 1-$NH_2$) are able to provide for skin rejuvenation and/or to reduce, prevent and/or eliminate skin imperfections, more precisely, the peptides of the present invention (as exemplified by Pal-SEQ ID NO: 1-$NH_2$) are able to provide for facial repositioning and/or facial skin tightening.

Example 11. Analysis of Cytotoxicity and Collagen Production of the Peptide Pal-SEQ ID NO: 1-$NH_2$ in Human Organotypical Skin Explant Cultures The cytotoxicity and collagen production of peptide Pal-SEQ ID NO: 1-$NH_2$ were analysed by means of the LDH cytotoxicity assay and the resazurin assay for cytotoxicity; and collagen content analysis and histological analysis with regard to collagen production.

Peptide Pal-SEQ ID NO: 1-$NH_2$ was prepared in accordance with examples 1 to 5.

In this case healthy and aged human organotypical skin explant cultures (hOSECs) were used as experimental systems.

The aged hOSEC was obtained by exposition of the healthy hOSEC to hydrocortisone (5 µg/mL) for the first five days of the study.

The total number of treatment groups was as follows:
1. Control group (negative control): Untreated hOSEC.
2. Aged hOSEC: hOSECs treated with hydrocortisone at 5 µg/mL (Abraham A, Roga G. (2014) *Topical steroid-damaged skin*. Indian J Dermatol. 59(5), 456-9.)
3. Aged hOSEC+Product A (cream, this is, placebo): hOSECs treated with hydrocortisone at 5 µg/mL and incubated with product A (10 µL).
4. Aged hOSEC+Product B (cream with Pal-SEQ ID NO: 1-$NH_2$ at a concentration of 0.005 mg/mL): hOSECs treated with hydrocortisone at 5 µg/mL and incubated with Product B (10 µL).

Four replicates of each experimental group were carried out and one independent experiment was performed.

The total duration of the assay was of 10 days (days 1 to 10). Hydrocortisone was applied in the appropriate or corresponding groups each day on days 1 to 5. On its side, Product B or Product A were applied in the corresponding or appropriate groups each day on days 2 to 9.

The cytotoxicity assays were performed on days 0 (before beginning the study), 1, 3, 5, 8 and 10.

Collagen production was measured on day 10.

LDH Cytotoxicity Assay

The LDH Cytotoxicity test is a colorimetric assay that quantitatively measures lactate dehydrogenase (LDH), a stable cytosolic enzyme that is released into the culture medium supernatant upon damage of the cytoplasmic membrane. The released LDH in culture medium supernatants is measured for 30 minutes coupled enzymatic reaction: LDH oxidizes lactate to pyruvate which then reacts with the tetrazolium salt WST-1 to form formazan. The increase in the amount of formazan measured in the culture supernatant directly correlates to the increase in the number of lysed cells (damage) in the skin explant.

100 µL supernatant of each sample were removed and transferred into a 96-well microplate. The released LDH in the culture medium supernatants was measured by a coupled enzymatic reaction: LDH oxidizes lactate to pyruvate which then reacts with the tetrazolium salt WST-1 to form formazan. The increase in the amount of formazan correlates directly with the increase in the number of lysed cells (damage) as the LDH enzyme is released into the culture medium supernatant when the cytoplasmic membrane is damaged. The formazan dye is water-soluble and can was measured using a standard ELISA plate reader at 500 nm.

The results of this assay were calculated considering the negative control, this is, untreated hOSEC as 100% of the LDH normal concentration. The results obtained appear summarized in FIG. 9.

As it is derivable from FIG. 9, values of LDH found in all the groups were similar to the Control group (negative control). This fact indicates that the hydrocortisone did not produce any adverse effect in hOSECs in the conditions of the assay (does not produce plasma membrane damage). Likewise, treatment with Product B (this is, cream with Pal-SEQ ID NO: 1-$NH_2$) or Product A and with hydrocortisone at 5 µg/mL did not show differences in LDH values with respect to the Control group. These data imply that hydrocortisone incubation and both compounds did not produce an adverse effect, plasma membrane damage, in hOSECs in the conditions of the assay.

Resazurin Assay

The resazurin dye (7-hydroxy-3H-phenoxazin-3-one 10-oxide) has been broadly used as an indicator of cell viability in proliferation and cytotoxicity assays. The assay is based on the ability of viable, metabolically active cells to reduce resazurin to resorufin and dihydroresorufin. This conversion is intracellular, facilitated by mitochondrial, microsomal and cytosolic oxidoreductases. Resazurin is non-toxic to cells and it is stable in culture medium. Therefore, it allows continuous measurement of cell proliferation in vitro as either a kinetic or an endpoint assay.

Resazurin dye, therefore, has been broadly used as an indicator of cell viability in several cytotoxicity assays. It is also a metabolic activity indicator as the assay is based on the ability of metabolically active cells to reduce resazurin to resorufin and dihydroresorufin by mitochondrial, microsomal and cytosolic oxidoreductases.

Toxic insult that impairs cell viability and proliferation also affects the capacity of cultures to reduce resazurin, and the rate of dye reduction is directly proportional to the number of viable cells present. Therefore, as the resazurin reduction is a direct measure of the metabolic competence of cell cultures, it provides a convenient index of cell viability. The decrease in the amount of resazurin reduced by hOSECs also directly correlates to the increase in the number of dead cells.

For the resazurin assay, the skin explants were treated with 6 µM of resazurin in NaCl solution for 1 hour. Subsequently, a volume of 100 µL of each sample was removed and transferred into a 96-well microplate. The resorufin formed was quantified in a fluorometer plate reader.

The fluorescent signal was monitored using 530-560 nm excitation wavelength and 590 nm emission wavelength.

The results of the resazurin assay were calculated considering the negative control, untreated healthy hOSECs, as 100% viability. The obtained results appear in FIG. 10.

A 10% reduction of Resorufin percentage was observed when the hOSECs were treated with 5 µg/mL of hydrocortisone with respect to the Control group (negative control). hOSECs treated with Product B (cream with Pal-SEQ ID NO: 1-$NH_2$) or Product A and with hydrocortisone at 5 µg/mL did not show a decrease of Resorufin values with respect to the Control group (negative control).

These data support the idea that both Product B or Product A produced a metabolic activation in hOSEC in the conditions of the assay. As the resorufin is a direct measure of metabolic competence of cells, resorufin increase may indicate a metabolic activation of the oxide-reductase enzymes following exposure of hOSECs to both compounds.

Therefore, from the results obtained in the LDH cytotoxicity assay and the resazurin assay it can be deduced that Pal-SEQ ID NO: 1-$NH_2$ was not toxic and, in fact, reverses the negative effects produced by hydrocortisone.

Collagen content analysis:

The Collagen Assay is a dye-binding method for the analysis of acid and pepsin-soluble collagens (mainly, Type I, but also types II, III, IV and V). The assay can assess the rate of newly synthesized collagen produced during periods of rapid growth and development.

Collagen Dye Reagent (1 mL) was added to each sample (tubes) and shaken for 30 minutes. The tubes were centrifuged at 12,000 rpm for 10 minutes. Subsequently, 750 µL ice-cold Acid-Salt Wash Reagent was added to the collagen-dye pellet to remove unbound dye from the surface of the pellet and from the inside surface of the microcentrifuge tube. The tubes were again centrifuged at 12,000 rpm for 10 minutes. Finally, 250 µL of alkali reagent was added. When all the bound dye was dissolved (5 minutes), the samples were ready for measurement. The dissolved dye (200 µL of each sample in 96 micro well plates) was measured using a standard ELISA plate reader at 550 nm.

As noted above, the collagen content analysis was performed on day number 10 of the study. The results of collagen content (micrograms) assay were calculated per milligram of fresh dermal tissue. The results obtained appear summarized in FIG. 11 and table 4.

TABLE 4

Collagen quantity in the different groups analysed in example 11.

| Group | Mean collagen quantity (in collagen µg/ skin mg) | Standard deviation (in collagen µg/ skin mg) |
| --- | --- | --- |
| Untreated hOSEC (Control group) | 0.863 | 0.09 |
| Aged hOSEC | 0.617 | 0.07 |
| Aged hOSEC + Product A | 0.610 | 0.06 |
| Aged hOSEC + Product B | 0.858 | 0.03 |

As shown in the FIG. 11 and table 4, an increase in the collagen production in the aged hOSEC treated with Product B (cream with 0.005 mg/mL of Pal-SEQ ID NO: 1-$NH_2$) was observed in comparison with the rest of aged hOSEC groups (only treated with hydrocortisone at 5 µg/mL or treated with hydrocortisone and Product A).

Group aged hOSEc+Product B, presented a collagen quantity similar to untreated hOSEC.

As noted in FIG. 11, the differences seen in collagen quantity between the groups of untreated hOSEC and aged hOSEC+Product B; and the groups of aged hOSEC and aged hOSEC+Product A are statistically significant. There was no statistically significant difference between untreated hOSEC and aged hOSEC+Product B.

These results demonstrate that the topical application of Pal-SEQ ID NO: 1-$NH_2$ reversed the hydrocortisone aging effects and, hence, demonstrate the potential of the peptides of the present invention (as exemplified by means of Pal-SEQ ID NO: 1-$NH_2$) as anti-ageing products and to prevent, reduce and/or eliminate the signs of aging as, for example, wrinkles, roughness and/or sagginess.

In addition, these results also demonstrate that the peptides of the present invention (as exemplified by Pal-SEQ ID NO: 1-$NH_2$) are able to provide for skin rejuvenation and/or to reduce, prevent and/or eliminate skin imperfections, more precisely, the peptides of the present invention (as exemplified by Pal-SEQ ID NO: 1-$NH_2$) are able to provide for facial repositioning and/or facial skin tightening.

Tissue collection and processing for TEM analysis:

Skin samples were processed for Transmission Electron Microscopy analysis. Briefly, skin samples were fixed in 4% (v/v) formaldehyde and 1% (v/v) glutaraldehyde. Subsequently, skin samples were incubated in sucrose 0.1 M overnight and in 1% (v/v) osmium tetroxide in 0.1 M. Finally, samples were dehydrated with serialized ethanol solutions and embedded in beam capsules.

Ultrathin sections (60-90 nm thick) were stained with uranyl acetate for 15 minutes and lead citrate for 5 minutes. Subsequently samples were ready to analyze under electron microscope.

Transmission electron microscopy study was performed to observe the state of collagen fibres in treated skin explants.

Results appear summarized in FIGS. 12A to 12D. FIG. 12A corresponds to an untreated hOSEC, and it displayed a correct dermal structure (complete and structured dermal fibres in dermis). Ukewise, FIG. 12B represents an aged hOSEC with unstructured collagen fibres (diffused, noncompact fibres). This image corroborated the adverse effect of hydrocortisone in skin which is in agreement with collagen quantification (included above). Similar image of non-compact collagen fibres was obtained for the aged skin treated with the Product A (FIG. 12C). However, as it can be seen in FIG. 12D, when aged hOSECs were incubated with Product B (cream with 0.005 mg/mL of peptide Pal-SEQ ID NO: 1-NH$_2$), a good regeneration of collagen fibres (complete and not diffused fibres) was achieved. This image corroborates the collagen values obtained by ELISA methods and noted above.

Likewise, collagen fibres thickness and collagen density were analysed by imagen analysis (see tables 5 and 6 below), and the values obtained corroborate the visual appreciations.

Collagen density indicates the compactness of each collagen fibre observed on the TEM image. To this end, the optical images were analyzed by GIMP2. The counterfactual analysis corroborated that healthy and aged hOSECs+Product B group presented density values higher than the values observed in aged hOSECs and aged hOSECs+Product A groups (see table 5 below and FIG. 13).

Group aged hOSEC+Product B (cream with 0.005 mg/mL of peptide Pal-SEQ ID NO: 1 NH$_2$), where it was appreciated an increase in collagen production, as noted above, presented a collagen density similar to untreated hOSEC (see table 5 below and FIG. 13).

TABLE 5

Collagen density in the different groups analysed in example 11.

| Group | Collagen density (in % with regard to untreated hOSEC) | Standard deviation (in %) |
|---|---|---|
| Untreated hOSEC (Control group) | 100 | 11.62 |
| Aged hOSEC | 82.22 | 6.54 |
| Aged hOSEC + Product A | 77.22 | 8.39 |
| Aged hOSEC + Product B | 95.56 | 3.63 |

As noted in FIG. 13, the differences seen in collagen density between the groups of untreated hOSEC and aged hOSEC+Product B; and the groups of aged hOSEC and aged hOSEC+Product A were statistically significant. There was no statistically significant difference between untreated hOSEC and aged hOSEC+Product B (cream with 0.005 mg/mL of peptide Pal-SEQ ID NO: 1-NH$_2$).

These results demonstrate that the topical application of Pal-SEQ ID NO: 1-NH$_2$ reversed the hydrocortisone aging effects and, hence, demonstrate the potential of the peptides of the present invention (as exemplified by means of Pal-SEQ ID NO: 1-NH$_2$) as anti-ageing products and to prevent, reduce and/or eliminate the signs of aging as, for example, wrinkles, roughness and/or sagginess.

In addition, these results also demonstrate that the peptides of the present invention (as exemplified by Pal-SEQ ID NO: 1-NH$_2$) are able to provide for skin rejuvenation and/or to reduce, prevent and/or eliminate skin imperfections, more precisely, the peptides of the present invention (as exemplified by Pal-SEQ ID NO: 1-NH$_2$) are able to provide for facial repositioning and/or facial skin tightening.

The collagen fibres thickness was also analyzed by GIMP2. The fibre thickness analysis corroborated that healthy and aged hOSEC+Product B (cream with 0.005 mg/mL of peptide Pal-SEQ ID NO: 1-NH$_2$) group presented fibre thickness values lower than the values observed in aged hOSEC and aged hOSEC+Product A groups due to a better compaction and structuration (complete and not diffused fibres). Pal-SEQ ID NO: 1-NH$_2$ peptide applied on aged hOSEC presented a collagen fibre thickness similar to untreated hOSEC (see table 6 and FIG. 14).

Higher fibres thickness in aged hOSEC and aged hOSEC+Product A groups indicated abnormal accumulation of collagen in the fibres which is described to occur in aged skin in vivo.

Untreated hOSEC and aged hOSEC+Product B showed similar thickness of collagen fibres.

TABLE 6

Collagen fibre thickness in the different groups analysed in example 11.

| Group | Collagen fibre thickness (nm) | Standard deviation (nm) |
|---|---|---|
| Untreated hOSEC (Control group) | 88.26 | 7.82 |
| Aged Skin | 98.77 | 8.44 |
| Aged Skin + Product A | 95.44 | 8.70 |
| Aged Skin + Product B | 84.87 | 6.85 |

As noted in FIG. 14, the differences seen in collagen fibre thickness between the groups of untreated hOSEC and aged hOSEC+Product B; and the group of aged hOSEC were statistically significant. The differences seen in collagen fibre thickness between the groups of untreated hOSEC and aged hOSEC+Product B; and the group of aged hOSEC+Product A were nearly statistically significant There was no statistically significant difference between untreated hOSEC and aged hOSEC+Product B (cream with 0.005 mg/mL of peptide Pal-SEQ ID NO: 1-NH$_2$).

These results demonstrate that the topical application of Pal-SEQ ID NO: 1-NH$_2$ reversed the hydrocortisone aging effects and, hence, demonstrate the potential of the peptides of the present invention (as exemplified by means of Pal-SEQ ID NO: 1-NH$_2$) as anti-ageing products and to prevent, reduce and/or eliminate the signs of aging as, for example, wrinkles, roughness and/or sagginess.

In addition, these results also demonstrate that the peptides of the present invention (as exemplified by Pal-SEQ ID NO: 1-NH$_2$) are able to provide for skin rejuvenation and/or to reduce, prevent and/or eliminate skin imperfections, more precisely, the peptides of the present invention (as exemplified by Pal-SEQ ID NO: 1-NH$_2$) are able to provide for facial repositioning and/or facial skin tightening.

Example 12. Clinical Evaluation of Skin and Wrinkle Smoothing and Antiaging Efficacy on Female Volunteers with Different Phototypes The effect of Pal-SEQ ID NO: 1-NH$_2$ peptide (synthesized in accordance with examples 1 to 5) on facial skin antiaging was evaluated on 44 female volunteers (50% light-pigmented (phototype II-III) and 50% dark-pigmented (phototype V-VI)).

Briefly, volunteers applied a cosmetic formulation with 2% (m/v) from a stock at 0.05% (m/v) of Pal-SEQ ID NO: 1-NH$_2$ or the cosmetic formulation without Pal-SEQ ID NO: 1-NH$_2$ (placebo). The application regime was of two times per day during 56 days, on early morning and before bedtime. Cosmetic formulation were applied on the whole face to compare the effect of placebo and active between volunteers and also between different phototype volunteers.

On days 28 and 56, an AEVA system was used on each volunteer in order to assess wrinkles depth and cheek roughness. A decrease of the parameters within the days of treatment indicated a smoothing of the skin, hence an antiwrinkle and antiaging benefit.

The results obtained are shown in FIG. 15.

As can be readily seen in FIGS. 15 (A) to (C), the cosmetic formulation comprising Pal-SEQ ID NO: 1-NH$_2$ showed decreases of either roughness (Ra) and relief (Rz) and wrinkle depth, on the region of facial skin studied in all studied times when compared to initial time (the decrease in some or all of these parameters shows a smoothing effect and a antiwrinkle and antiaging effect) and for all the skin phototypes studied. As much as 4% decrease in cheek roughness (5% average versus placebo) and 7% decrease in cheek relief (10% average versus placebo) was seen after 56 days of treatment. For wrinkles depth a more pronounced effect was observed reaching a 9% decrease in average, especially for the volunteers with a phototype V-VI skin were a 12% decrease in the depth of the wrinkles was observed (20% versus placebo) while volunteers with phototype II-III skin experienced a 6-7% of decrease in wrinkles depth with time.

The invention claimed is:

1. A tetrapeptide of formula (I):

$$R_1\text{-His-Tyr-Arg-Ala-}R_2(R_1\text{-SEQ ID NO: 1-}R_2) \quad (I),$$

or a cosmetically acceptable isomer, salt or solvate thereof, wherein:

"R$_1$ is selected from the group consisting of H, substituted or unsubstituted non-cyclic aliphatic group," substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group consisting of substituted or unsubstituted C$_1$-C$_{24}$ alkyl radical, substituted or unsubstituted C$_2$-C$_{24}$ alkenyl, substituted or unsubstituted C$_2$-C$_{24}$ alkynyl, substituted or unsubstituted C$_3$-C$_{24}$ cycloalkyl, substituted or unsubstituted C$_5$-C$_{24}$ cycloalkenyl, substituted or unsubstituted C$_8$-C$_{24}$ cycloalkynyl, substituted or unsubstituted C$_6$-C$_{30}$ aryl, substituted or unsubstituted C$_7$-C$_{24}$ aralkyl, substituted or unsubstituted heterocyclyl ring of 3 to 10 atoms, and substituted or unsubstituted heteroarylalkyl of 2 to 24 carbon atoms and 1 to 3 atoms other than carbon and an alkyl chain of 1 to 6 carbon atoms; and R$_2$ is selected from the group consisting of H, —NR$_3$R$_4$—, —OR$_3$ and —SR$_3$, wherein R$_3$ and R$_4$ are

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Artificially synthesized sequence

<400> SEQUENCE: 1

His Tyr Arg Ala
1

<210> SEQ ID NO 2
<211> LENGTH: 4
<212> TYPE: PRT
<213> ORGANISM: Artificial Sequence
<220> FEATURE:
<223> OTHER INFORMATION: Artificially synthesized sequence
<220> FEATURE:
<221> NAME/KEY: VARIANT
<222> LOCATION: 2
<223> OTHER INFORMATION: Xaa is selected from the group of amino acids
      with an aromatic side-chain
<220> FEATURE:
<221> NAME/KEY: VARIANT
<222> LOCATION: 3
<223> OTHER INFORMATION: Xaa is selected from Lys or Arg
<220> FEATURE:
<221> NAME/KEY: VARIANT
<222> LOCATION: 4
<223> OTHER INFORMATION: Xaa is selected from the group of amino acids
      with an aliphatic non-polar side-chain

<400> SEQUENCE: 2

His Xaa Xaa Xaa
1 independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl.

2. The tetrapeptide in accordance with claim 1, wherein $R_1$ is palmitoyl group (Pal) or acetyl group (Ac).

3. The tetrapeptide in accordance with claim 1, wherein $R_2$ is H or $NH_2$.

4. The tetrapeptide in accordance with claim 1, wherein $R_1$ is Pal and $R_2$ is $NH_2$.

5. The tetrapeptide in accordance with claim 1, wherein the tetrapeptide of formula (1) is:

Pal-His-Tyr-Arg-Ala-$NH_2$(Pal-SEQ ID NO: 1-$NH_2$).

6. A cosmetic composition comprising the tetrapeptide of claim 1 or a cosmetically acceptable isomer, salt or solvate thereof.

7. A method for rejuvenating skin, reducing signs of skin aging and/or eliminating skin imperfections in a subject in need thereof, wherein the method comprises applying to said subject the cosmetic composition of claim 6.

8. The method of claim 7, wherein the signs of skin aging are wrinkles, roughness and/or sagginess.

9. The method of claim 7, wherein applying the cosmetic composition results in skin firming, body sculpturing, facial repositioning, skin tightening and/or pore refining in the subject.

* * * * *